United States Patent
Ferro et al.

(10) Patent No.: US 12,315,642 B2
(45) Date of Patent: May 27, 2025

(54) SYSTEMS, METHODS, AND DEVICES FOR VIRTUALLY SUPERVISED MEDICAL WEIGHT LOSS TREATMENT PROGRAM ADMINISTERED VIA ON-DEMAND TELEHEALTH PROCTOR-OBSERVED PLATFORM

(71) Applicant: EMED LABS, LLC, Miami, FL (US)

(72) Inventors: Michael W. Ferro, Palm Beach, FL (US); Colman Thomas Bryant, Fort Lauderdale, FL (US)

(73) Assignee: EMED LABS, LLC, Miami, FL (US)

( * ) Notice: Subject to any disclaimer, the term of this patent is extended or adjusted under 35 U.S.C. 154(b) by 0 days.

(21) Appl. No.: 18/325,812

(22) Filed: May 30, 2023

(65) Prior Publication Data

US 2023/0386677 A1   Nov. 30, 2023

Related U.S. Application Data

(60) Provisional application No. 63/491,701, filed on Mar. 22, 2023, provisional application No. 63/485,513, (Continued)

(51) Int. Cl.
*G16H 50/50* (2018.01)
*G06T 7/60* (2017.01)
(Continued)

(52) U.S. Cl.
CPC ............... *G16H 50/50* (2018.01); *G06T 7/60* (2013.01); *G06T 17/00* (2013.01); *G16H 20/10* (2018.01);
(Continued)

(58) Field of Classification Search
CPC ........ G16H 50/50; G16H 20/10; G16H 80/00; G16H 50/20; G06T 7/60; G06T 17/00;
(Continued)

(56) References Cited

U.S. PATENT DOCUMENTS

| | | |
|---|---|---|
| 11,211,162 B1 | 12/2021 | Weiler et al. |
| 11,289,196 B1 | 3/2022 | Ferro, Jr. et al. |

(Continued)

FOREIGN PATENT DOCUMENTS

WO    WO-2020023289 A1 *   1/2020    ............. G16H 20/17

OTHER PUBLICATIONS

International Search Report and Written Opinion for Application No. PCT/US2023/023888 dated Aug. 31, 2023 in 15 pages.

*Primary Examiner* — Robert A Sorey
*Assistant Examiner* — Kimberly A. Sass
(74) *Attorney, Agent, or Firm* — Perkins Coie LLP

(57) ABSTRACT

Disclosed herein are systems, methods, and devices for an image-based, computer vision approach for anthropometric measurement of a user using an automatically generated three-dimensional model of the user. Also disclosed herein are systems, methods, and devices associated with a telehealth proctoring platform that can be used to remotely proctor, monitor, and manage patients over the course of a medical treatment plan. The telehealth proctoring platform may be used to collect and retrieve various kinds of data associated with a patient, such as at-home diagnostic test data, the anthropometric measurements of the patient, or the generated three-dimensional models in order to remotely monitor and track changes to the body of a patient over time and make dynamic adjustments to the patient's medical treatment plan.

20 Claims, 9 Drawing Sheets

Related U.S. Application Data filed on Feb. 16, 2023, provisional application No. 63/365,461, filed on May 27, 2022, provisional application No. 63/365,441, filed on May 27, 2022.

(51) Int. Cl.
| | | |
|---|---|---|
| *G06T 17/00* | (2006.01) | |
| *G16H 20/10* | (2018.01) | |
| *G16H 80/00* | (2018.01) | |
| *G16H 50/20* | (2018.01) | |

(52) U.S. Cl.
CPC ... *G16H 80/00* (2018.01); *G06T 2207/30004* (2013.01); *G06T 2207/30196* (2013.01); *G06T 2210/41* (2013.01); *G16H 50/20* (2018.01)

(58) Field of Classification Search
CPC . G06T 2207/30004; G06T 2207/30196; G06T 2210/41
USPC .............................................................. 705/2
See application file for complete search history.

(56) References Cited

U.S. PATENT DOCUMENTS

| | | | |
|---|---|---|---|
| 2017/0303886 A1 | 10/2017 | Ferro, Jr. | |
| 2018/0253840 A1* | 9/2018 | Tran | G16H 40/63 |
| 2021/0202104 A1* | 7/2021 | Bostic | G16H 50/30 |
| 2022/0084665 A1* | 3/2022 | Blackburn | G16H 40/67 |
| 2022/0319676 A1* | 10/2022 | Bosanac | G16H 70/40 |

* cited by examiner

SYSTEMS, METHODS, AND DEVICES FOR VIRTUALLY SUPERVISED MEDICAL WEIGHT LOSS TREATMENT PROGRAM ADMINISTERED VIA ON-DEMAND TELEHEALTH PROCTOR-OBSERVED PLATFORM

CROSS-REFERENCE TO RELATED APPLICATIONS

This application claims the benefit of U.S. Provisional Patent Application No. 63/491,701, entitled "SYSTEMS, METHODS, AND DEVICES FOR VIRTUALLY SUPERVISED MEDICAL WEIGHT LOSS TREATMENT PROGRAM ADMINISTERED VIA ON DEMAND TELEHEALTH PROCTOR-OBSERVED PLATFORM," filed Mar. 22, 2023, the contents of which are incorporated by reference herein in their entirety. This application also claims the benefit of U.S. Provisional Patent Application No. 63/485,513, entitled "SYSTEMS, METHODS, AND DEVICES FOR COMPUTER IMAGE-BASED BODY MEASUREMENT AND TRACKING," filed Feb. 16, 2023, the contents of which are incorporated by reference herein in their entirety. This application also claims the benefit of U.S. Provisional Patent Application No. 63/365,441, entitled "IMAGE-BASED BODY MEASUREMENT AND TRACKING," filed May 27, 2022, the contents of which are incorporated by reference herein in their entirety. This application also claims the benefit of U.S. Provisional Patent Application No. 63/365,461, entitled "IMAGE-BASED BODY MEASUREMENT AND TRACKING," filed May 27, 2022, the contents of which are incorporated by reference herein in their entirety.

TECHNICAL FIELD

The present application is directed to systems, methods, and devices for image-based body measurement and tracking, which can be used to monitor and track patients over time, such as patients engaged in a medical treatment plan. Thus, some embodiments of the application are further directed to systems, methods, and devices associated with a telehealth proctoring platform that can be used to remotely monitor, track, consult, and manage patients over the course of a medical treatment plan (e.g., a weight loss treatment program).

BACKGROUND

Over the course of a medical treatment plan, a patient may have to periodically check-in with a medical professional through in-person appointments, so that medication can be administered, procedures or exercises can be performed, measurements or tests can be taken, the patient's progress can be tracked, and compliance with the medical treatment plan can be determined. However, this can be quite inconvenient, costly, and time-consuming since the patient may have to regularly set aside time for traveling and consulting the medical professional in-person.

Telehealth alleviates some of these problems by enabling long-distance contact between the patient and a medical professional. Through a conventional telehealth platform, a medical professional may be able to remotely provide care and advice to a patient. The medical professional may even be able to remotely prescribe a medication or a treatment plan for the patient.

However, it can be difficult to remotely collect accurate patient data, such as test results or anthropometric measurements over a conventional telehealth platform. For example, accurate test results can be difficult to obtain without the use of expensive laboratory equipment, and patients provided with at-home, self-administered diagnostic tests may provide inaccurate results (e.g., due to not properly following procedures and protocol). As another example, accurate anthropometric measurements can be difficult to obtain without the use of expensive three-dimensional body scanners. Alternatively, tasking a patient with manually providing measurements of their body will often provide inaccurate results (e.g., due to the difficulty of correctly aligning a measuring tape around the body, measuring the same location on the body each time a measurement is taken, and correctly reading the measurement once the measuring tape is in place). This can make it difficult to monitor/track changes to the patient's body over time, and the changes to the patient's body over time may provide valuable insights in certain contexts (e.g., a weight loss program), such as to determine if the patient is compliant with a treatment plan or if the treatment plan needs to be adjusted.

Thus, there exists a need for an inexpensive and accurate approach for remotely collecting a patient's test results or anthropometric measurements in order to monitor or track the changes to a patient's body over time.

SUMMARY

For purposes of this summary, certain aspects, advantages, and novel features are described herein. It is to be understood that not necessarily all such advantages may be achieved in accordance with any particular embodiment. Thus, for example, those skilled in the art will recognize the disclosures herein may be embodied or carried out in a manner that achieves one or more advantages taught herein without necessarily achieving other advantages as may be taught or suggested herein.

All of the embodiments described herein are intended to be within the scope of the present disclosure. These and other embodiments will be readily apparent to those skilled in the art from the following detailed description, having reference to the attached figures. The invention is not intended to be limited to any particular disclosed embodiment or embodiments.

This application describes systems, methods, and devices that can solve or alleviate problems with current methods of anthropometric measurements by utilizing image-based computer vision techniques to facilitate the remote anthropometric measurement of a user using an automatically generated three-dimensional model of the user. These models and measurements can be used to remotely monitor and track the body of a patient over time, such as a patient engaged in a medical weight loss program or a medical treatment plan. For example, weight loss, weight gain, and muscle gain can be tracked using anthropometric measurement of body parts. Additionally, the anthropometric measurement of body parts can also be used to yield valuable insights regarding the health of the patient. For example, a high waist circumference has been shown to correlate with health risks such as high blood pressure, high cholesterol, heart disease, and type-2 diabetes.

Accordingly, this application also describes systems, methods, and devices associated with a telehealth proctoring platform that can be used to remotely proctor, monitor, and manage a patient over the course of a medical treatment plan (e.g., a weight loss treatment program). In some embodiments, the telehealth proctoring platform may be used to initiate and establish virtual proctoring sessions between a patient and a proctor, thereby providing proctored supervision for a variety of scenarios, such as the administration of medication, performance of procedures or exercises, taking measurements or tests, and tracking of patient progress and compliance. The platform may be able to utilize the three-dimensional models and anthropometric measurements of the patient to remotely monitor and track changes to the body of a patient over time. Furthermore, other kinds of patient data such as test results may also be remotely collected from the patient (e.g., with the use of at-home blood collection devices and/or other home diagnostic devices, such as A1C tests) via telehealth proctored supervision, and the platform may be able to also utilize the test results to remotely monitor and track changes to the body of a patient over time.

In some embodiments, an anthropometrically correct three-dimensional model of a user may be created based on images of the user captured by a camera of a user computing device. In some embodiments, a three-dimensional model of a user may be generated based on a set of images that capture the user in multiple poses. This collection process may be performed multiple times over a period of time (e.g., resulting in multiple sets of images) and used to generate multiple three-dimensional models or provide the user a numerical or graphical representation of a change of the user's body over the period of time. In some embodiments, images of the user can be overlaid onto the three-dimensional model so that it is a better digital representation of the user.

In some embodiments, the telehealth proctoring platform can be used for supervised medical weight loss treatment, and the platform may be configured to at least in part automatically create an anthropometrically correct three-dimensional model of a patient based on images of the patient to assist in monitoring, proctoring, or educating a patient in administering pharmaceuticals and/or following a dietary plan that enable a patient to lose weight. In some embodiments, the platform may be able to provide behavioral or other health recommendations to the patient based on the three-dimensional model, inputs or goals provided by the patient, and/or generally accepted medical thresholds. In some embodiments, the platform may be able to generate and provide a predictive three-dimensional model that digital represents the patient's body at a future point in time based on the patient's goals and/or a current progress of the patient over time.

In some embodiments, the systems disclosed herein can be configured to enable a telehealth proctoring platform that is available 24/7 on-demand to patients and other users, such as proctors and clinicians (e.g., for the observing and reporting of a patient that desires to register for or is participating in a medical weight loss program that is being monitored and/or administered and/or proctored using the platform). In some embodiments, the systems disclosed herein can be configured to enable an on-demand proctoring platform that is available 24/7 to allow patients to visit with a proctor and/or a clinician and/or conduct a supervised medical weight loss session on-demand, such that no preset or previously scheduled appointments for an initial consultation and/or subsequent consultations are required for the patient.

In some embodiments, the systems disclosed herein can be configured to enable a telehealth proctoring platform that is available 24/7 on-demand to enable patients to conduct an initial consultation for enrolling into a medical treatment plan such as a medical weight loss program. In some embodiments, the systems disclosed herein enable a proctor and/or a clinician to guide a patient through a treatment process and/or instruct and/or monitor and/or proctor a patient through the administration of drugs, such as weight loss medication/injections, to the patient.

In some embodiments, the systems disclosed herein can be configured to conduct an initial intake of patient information via an online registration system (un-proctored or proctored), and in some embodiments, the systems disclosed herein can receive the initial intake patient information and connect the patient via an on-demand 24/7 consultation platform that enables a patient to virtually speak with a proctor and/or medical professional in a telehealth session to discuss and/or confirm patient medical eligibility and/or insurance eligibility for a medical weight loss treatment program. I In some embodiments, the systems disclosed herein can be configured to enable a platform for the observing and reporting of a patient that is under a weight loss program that is being monitored and/or administered and/or proctored using the platform. In some embodiments, the systems disclosed herein can be configured to observe and/or report weight loss associated with a patient that is under a weight loss program. In some embodiments, the systems disclosed herein can be configured to enable an on-demand telehealth proctoring platform that is available 24/7 to patients and users for the observing and reporting of a patient that desires to register for or is participating in a weight loss program that is being monitored and/or administered and/or proctored using the platform.

In some embodiments, the systems disclosed herein can be configured to enable an on-demand proctoring platform that is available 24/7 to connect the patient with, in some cases, immediately after the patient enters the registration data, an on-demand insurance review platform that is available 24/7 to determine whether the patient is eligible for insurance reimbursement for a weight loss program. In some embodiments, the systems disclosed herein can be configured to enable an on-demand proctoring platform that is available 24/7 to connect the patient with a live proctor wherein the platform is configured to allow the patient to show the patient's driver's license and/or insurance card to the live proctor as part of an on-demand, 24/7 available intake process. In some embodiments, the systems disclosed herein can be configured to enable an on-demand proctoring platform that is available 24/7 to determine if a patient requires a lab and/or blood test and/or other test such that the on-demand, 24/7 available platform can generate a lab appointment for the patient in real-time or substantially real-time. In some embodiments, the systems disclosed herein can be configured to enable an on-demand proctoring platform that is available 24/7 to determine that a patient is eligible and/or has received insurance approval for joining a supervised medical weight loss program, such that the system can be configured to connect the patient with a physician on-demand and 24/7.

In some embodiments, the systems disclosed herein can be configured to enable an on-demand proctoring platform that is available 24/7 to enable the physician to see patient data and/or insurance approval and/or patient medical eligibility, and/or weight loss treatment program details, and/or data relating to medical prescription drugs alongside with a video display of the patient in order to provide the patient with eligibility information and/or approval information for prior authorization, and/or medication process information, for example, when and how the patient will receive medication and what is the process over a period of time, for example, next 4 weeks, and/or how to administer medication, for example, inject once a week with a supervised proctor monitoring to ensure that the patient is doing it correctly, wherein the on-demand 24/7 platform is configured to enable recording of the supervised sessions in order to enable future audits of patient sessions, wherein the audit data enables the patient to qualify and keep eligibility for refills of the medication.

In some embodiments, the systems disclosed herein can be configured to enable an on-demand proctoring platform that is available 24/7 to provide the physician with a checklist to ensure that the clinician is providing all necessary medical information to reduce liability and/or to enable the physician to check off that the patient is in compliance with the drug treatment program and/or to enable the physician to check off that the patient remains eligible for additional medication.

In some embodiments, the systems disclosed herein can be configured to enable an on-demand proctoring platform that is available 24/7 to enable a proctor and/or a physician to provide to patients in real-time guidance, instructions, information and the like regarding the administration of drugs, such weight loss medication and/or injections, and in some embodiments, the systems disclosed herein can enable the proctor and/or physician to observe and report on the administration of medication to the patient in order to generate audit data and/or to ensure treatment compliance, which can be used to make the patient eligible for future medication to be administered to the patient as part of the treatment program.

In some embodiments, the systems disclosed herein can be configured to enable an on-demand proctoring platform that is available 24/7 to allow patients to visit with a proctor and/or a physician and/or conduct a supervised medical weight loss session on-demand, 24/7 such that no preset or previously scheduled appointments for an initial consultation and/or subsequent consultations are required for the patient. In some embodiments, the systems disclosed herein can be configured to enable an on-demand proctoring platform that is available 24/7 to enable patients to conduct an initial consultation through an on-demand, 24/7 platform that allows the patient to register for a supervised medical weight loss program that provides access to medical prescription drugs and/or enables a patient to join a weight loss program, by allowing the patient to input demographics information, body mass index (BMI) information, other conditions, A1C status, and any other patient information necessary or desirable for determining a patient's eligibility for the weight loss treatment program.

Embodiments of the inventions described herein can comprise several novel features and no single feature is solely responsible for the desirable attributes or is essential to practicing the inventions described.

For purposes of this summary, certain aspects, advantages, and novel features of the invention are described herein. It is to be understood that not necessarily all such advantages can be achieved in accordance with any particular embodiment of the invention. Thus, for example, those skilled in the art will recognize that the invention can be embodied or carried out in a manner that achieves one advantage or group of advantages as taught herein without necessarily achieving other advantages as can be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the disclosure are described with reference to drawings of certain embodiments, which are intended to illustrate, but not to limit, the present disclosure. It is to be understood that the accompanying drawings, which are incorporated in and constitute a part of this specification, are for the purpose of illustrating concepts disclosed herein and may not be to scale.

DETAILED DESCRIPTION

Figure 1B:
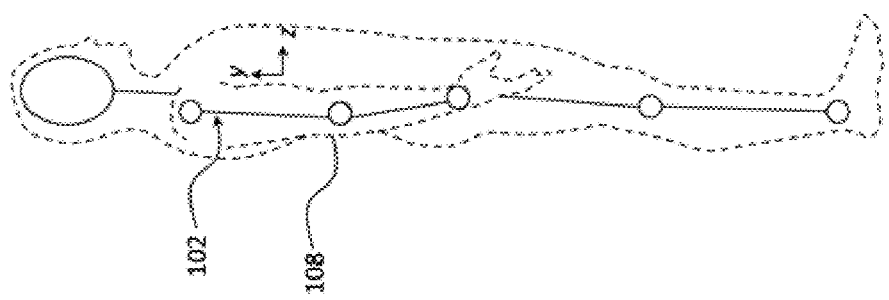
FIG. 1B illustrates a side view of the three-dimensional model of FIG. 1A.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

As mentioned briefly above and as will now be explained in more detail below, this application describes computer-vision based systems, methods, and devices configured to facilitate anthropometric measurement of a user using an automatically generated three-dimensional model of the user. These models and measurements can be used to remotely monitor patients over time, such as patients engaged in a medical weight loss program or a medical treatment plan.

Accordingly, this application also describes systems, methods, and devices associated with a telehealth proctoring platform that can be used to remotely proctor, monitor, and manage patients over the course of a medical treatment plan (e.g., a weight loss treatment program) by leveraging three-dimensional models and anthropometric measurements of the patients. The platform may be able to utilize the three-dimensional models and anthropometric measurements of the patient to remotely monitor and track changes to the body of a patient over time. Furthermore, other kinds of patient data such as test results may also be remotely collected from the patient (e.g., with the use of at-home blood collection devices and/or other home diagnostic devices, such as A1C tests) via telehealth proctored supervision, and the platform may be able to also utilize the test results to remotely monitor and track changes to the body of a patient over time.

Embodiments of the inventions described herein can comprise several novel features and no single feature is solely responsible for the desirable attributes or is essential to practicing the inventions described.

Anthropometric Measurement and 3D Models

Typically, accurate anthropometric measurements can be difficult to obtain, without the use of expensive three-dimensional body scanners. Further, taking anthropometric measurements at home manually often provides inaccurate results due to the difficulty of correctly aligning a measuring tape around the body, measuring the same location on the body each time a measurement is taken, and correctly reading the measurement once the measuring tape is in place. As described herein, computer-vision based anthropometric measurement can solve or alleviate problems with current methods of anthropometric measurements.

In some embodiments, the systems, methods, and devices described herein can facilitate anthropometric measurement. In some embodiments, the system can include a mobile or web-based application configured to run on a user device. The user device can be a smartphone, tablet, laptop, desktop computer, or any other personal computing device. The application can perform image-based anthropometric measurements of a user via one or more cameras of the user computing device. In some embodiments, the one or more cameras of the user computing device can be omnidirectional cameras. In some embodiments, the user device can include one or more depth sensors. In some embodiments, the one or more depth sensors can include one or more light detection and ranging (LIDAR) sensors.

In some embodiments, the system can provide instructions to the user. The instructions can include instructing the user to position user device such that at least a portion of the user is in view of the one or more cameras and/or the one or more depth sensors. In some embodiments, the instructions can include instructing the user to move to a position or a location such that at least the portion of the user is in view of the one or more cameras and/or the one or more depth sensors.

In some embodiments, the system can take photos and/or videos of the users. The system can automatically and dynamically analyze image data from the photos and/or videos in order to determine whether the portion of the user is in view of the one or more cameras and/or the one or more depth sensors. In some embodiments, the system can determine if the user's entire body is in view of the one or more cameras and/or depth sensors. In some embodiments, if the portion of the user or the user's entire body is not in view of the one or more cameras and/or depth sensors, the system can instruct the user to move in one or more directions until the user the portion of the user or the user's entire body is in view of the one or more cameras and/or depth sensors. The system can instruct the user via sound generated by a speaker or other audio device of the user device and/or computer-generated graphics displayed on a display of the user device. In some embodiments the computer-generated graphics can include at least one of augmented reality or virtual reality content displayed on the display of the user computing device. The computer-generated graphics can be displayed on the display of the user computing device on top of a live video feed or other images captured by the one or more cameras and/or depth sensors of the user device.

In some embodiments, the system can instruct the user to stand, sit, and/or lay in one or more poses. The system can instruct the user to stand in a first pose. The one or more cameras and/or depth sensors can capture one or more images, depth data and/or other image data of the user in the first pose. In some embodiments, the system can capture one or more images, depth data and/or other image data of the user in one or more second poses. The first pose and one or more second poses can depend on which area of the body or body part the system intends to capture one or more images or other image data of.

In some embodiments, the system can instruct the user to perform one or more movements in one or more of the first pose or the one or more second poses. For example, the system can instruct the user to stand in the first pose and the system can instruct the user to perform a 360-degree spin. The system can capture one or more images, depth data, and/or other image data of the user performing the one or more movements. In some embodiments, the system can automatically and dynamically create one or more subsets of data that each include one or more of the captured one or more images, depth data, and/or other image data based on one or more key poses of the user. The system can automatically analyze the one or more images, depth data, and/or other image data and in order to automatically determine when the user is performing the one or more key poses. For example, the system can automatically determine when a user has spun 90-degree 180-degrees, and 270-degrees.

In some embodiments, the system can automatically and dynamically analyze the one or more images, depth data, and/or other image data in order to determine if the system captured a minimum amount of data. If the system did not capture a minimum amount of data, the system can instruct the user to perform one or more of the second poses, or the system can instruct the user to repeat the first pose and the one or more movements until the system captures the minimum amount of data.

In some embodiments the system can automatically and dynamically process the one or more images, depth data and/or other image data in order to create one or more digital representations of the user.

Figure 1A:
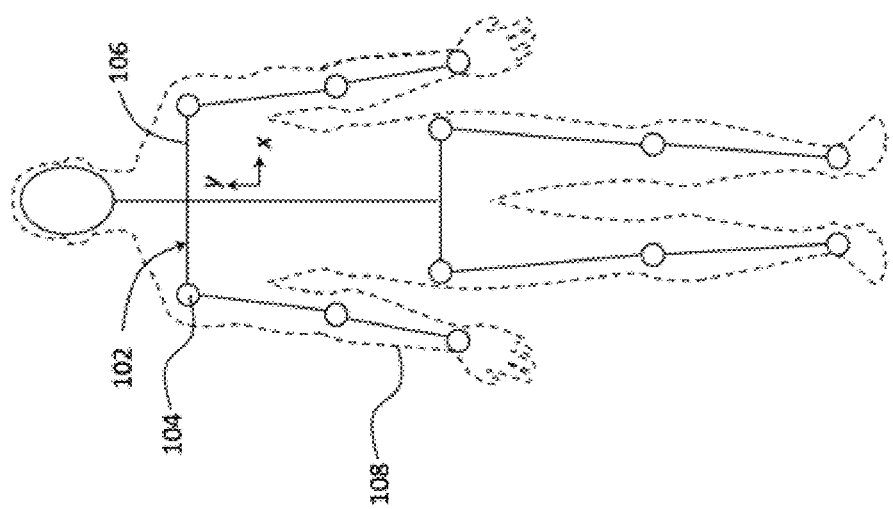
FIG. 1A illustrates a front view of an example three-dimensional model of an embodiment of the present application.

As shown in FIGS. 1A and 1B, the one or more digital representations can include a user skeleton 102, which may represent, in a schematic or simplified manner, one or more portions of the user's anatomy. The user skeleton 102 can include one or more joints 104 and one or more lines 106. The one or more joints 104 can correspond to a location of the user's joints, and the one or more lines 106 can correspond to a location of the user's bones or skeleton. In some embodiments, the lines 106 can be substantially straight lines connecting the joints 104. In some embodiments, the user skeleton 102 can be based on motion of the user automatically detected by the system in the one or more images, depth data, and/or other image data. In some embodiments, the system can map the user skeleton 102 onto one or more of the subsets of data.

In some embodiments, the one or more digital representations can include one or more three-dimensional models 108 of the user. The three-dimensional model 108 of the user can be a generic three-dimensional model or the three-dimensional model 108 can include one or more images of the user overlayed on the three-dimensional model 108 such that the three-dimensional model 108 resembles the user. In some embodiments, the system can capture one or more model images, such as an image of the user's face, in order to create a high-resolution model. In some embodiments, the three-dimensional model 108 can be a representation of the user's body at the time the system captures the one or more images, depth data, and/or other image data. The three-dimensional model 108 can represent the user's height, weight and/or body proportions.

In some embodiments, the user can select one or more portions of the three-dimensional model 108 as a reference point. The system can display information associated with the one or more portions of the three-dimensional model 108. For example, the system can show a user bicep circumference, waist size, or any other body size measurement.

Figure 2:
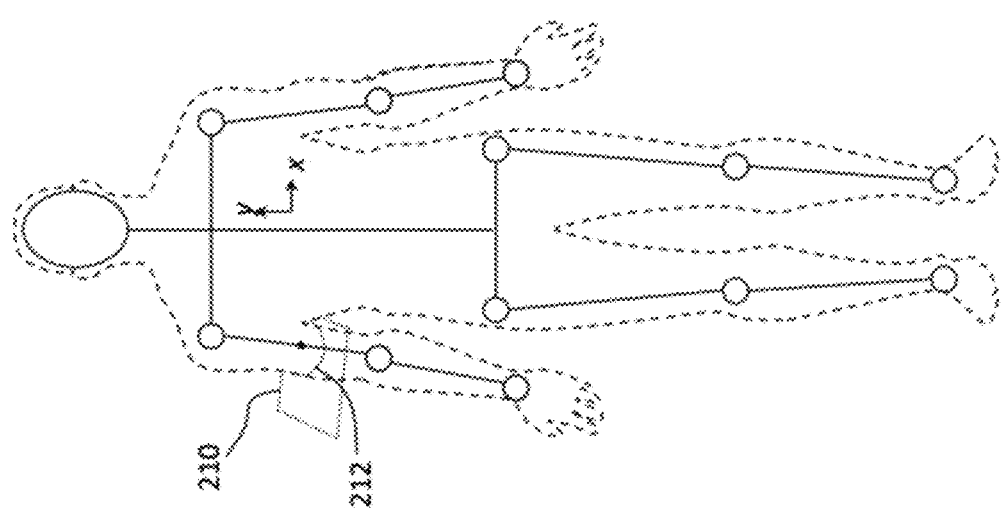
FIG. 2 illustrates a front view of an example three-dimensional model of an alternative embodiment of the present application.

As shown in FIG. 2, the system can automatically determine the information associated with the one or more portions of the three-dimensional model 108. In some embodiments, the system can automatically determine the reference point based on the user's desired measurement of a body part. The system can automatically determine a point on one of the lines 106 associated with the body part. For example, if the user selects measurement of a bicep, the system can automatically determine a halfway point between a shoulder joint of the model and an elbow joint of the model as the reference point. In some embodiments, the system can determine a point on the line 106 associated with the body part relative to the ground. For example, if the user selects a measurement of the user's waist, the system can always measure the user's waist at a same height from the ground. The system can automatically and dynamically generate a measurement plane 210 at the reference point. The measurement plane 210 can extend from the reference point substantially perpendicularly to the line 106. In some embodiments, the reference point can extend from the reference point at any angle relative to the line 106. The angle relative to the line 106 can depend on which body part the user selects and/or which measurement of the body part the user selects. A measurement can be automatically calculated by the system by determining a line 212 where the measurement plane 210 intersects with the three-dimensional model 108. In some embodiments, the measurement can be a global measurement of the body. For example, the system can be able to automatically measure the user's height, BMI, or any other global measurement.

Figure 3:
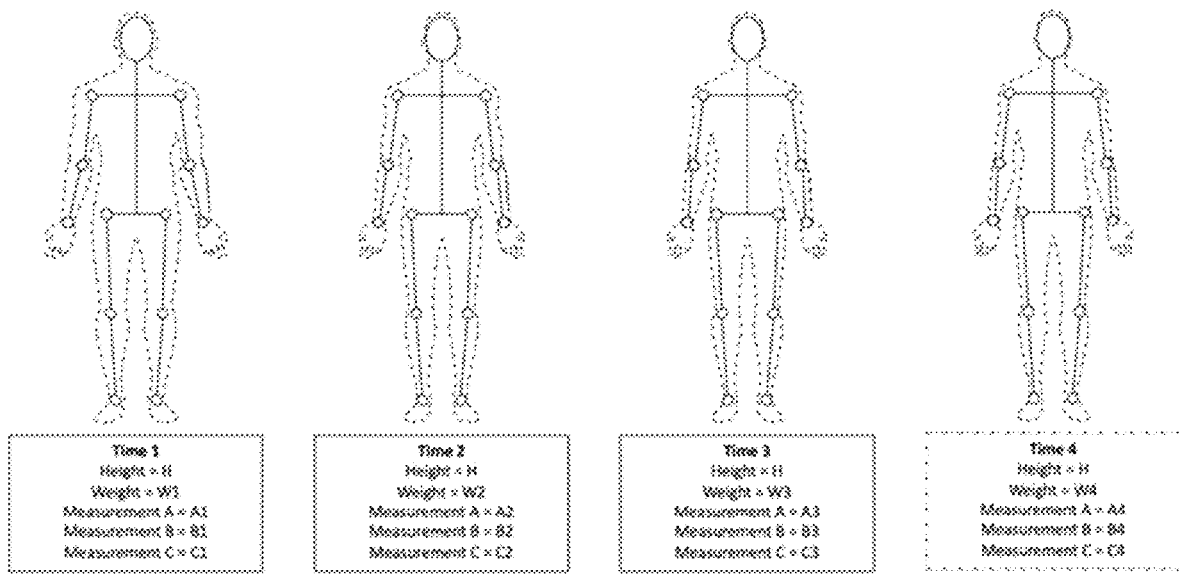
FIG. 3 illustrates a front view of a plurality of example three-dimensional models of an embodiment of the present application.

In some embodiments, the system can capture one or more images, depth data, and/or other image data multiple times over a period of time. In these embodiments, as shown in FIG. 3, the system can display measurements associated with the one or more portions of the three-dimensional model 108 over time. The system can perform measurements each time the system captures the one or more images, depth data, and/or other image data. The skeleton 102 can remain substantially the same over time because the user's skeleton may not change with weight gain or weight loss. Therefore, the reference point for each measurement can remain substantially the same over time.

In some embodiments, the system can display information numerically. The system can display a graph of the information over time, a total change in the information, a table of the information over time, and/or any other numerical representation of the information over time. In some embodiments, the system can display a change in the three-dimensional model 108 over time. For example, the system can display a time lapse of the three-dimensional model 108, or a portion of the three-dimensional model 108 over time in order to show the user how the user's body has changed over time.

In some embodiments, the system can automatically and dynamically generate a predictive three-dimensional model. The predictive three-dimensional model can show the user what the user's body may look like in the future. In some embodiments, the predictive three-dimensional model can be based on input targets. The predictive model can be based one or more current user inputs and/or one or more input targets. The one or more current user inputs can include at least one of, the user's weight, the user's body fat percentage, food log, exercise logs, sleep habits, resting heart rate, blood pressure, or any other metric. The input target can include at least one of a desired body fat percentage, muscle percentage, overall weight, measurements at the reference point, or any other metric. In some embodiments, the predictive three-dimensional can display to the user what the user will look like if the user continues with inputs similar to the one or more current user inputs. In some embodiments, the predictive three-dimensional model can display to the user what the user will look like if the user reaches the input target. In some embodiments, the system can display one or more sliders with the predictive three-dimensional model. Each slider can be associated with one or more of target inputs. The user can adjust the sliders, and the system can automatically and dynamically adjust the predictive three-dimensional model.

In some embodiments, the system can provide recommendations to the user. The recommendations can be based on one or more of the one or more current user inputs, the input targets, the predictive three-dimensional model, or medical thresholds. The medical thresholds can include target BMI, waist circumference, weight generally considered to be healthy. The recommendations can include behavioral recommendations such as eating habits, sleep habits, exercises or any other lifestyle or behavioral changes. In some embodiments, the recommendations can include nutritional information such as recommended daily caloric intake and/or recommended daily macros. In some embodiments, the system can connect the user with a healthcare provider. The system can connect the user to the healthcare provider by telephone, email, in-person appointment, or a telehealth session.

In some embodiments, the system can send alerts to the user device. The alerts can include one or more notifications, reminders and/or alarms. The alerts can include reminders about exercise routines, the user's nutritional goals, rewards for completing an exercise or hitting the target input, words of encouragement, and/or any other information. In some embodiments, the system can determine the user's location based on one or more location sensors of the user device. The system can, based on the user's location, send custom alerts to the user device. For example, if the system determines the user is at a grocery store, the system can send suggested foods or recipes, or nutritional information to the user device. The system can be configured to automatically keep track of when the user goes to a gym based on the user's location.

In some embodiments, the system can automatically determine a number of steps the user takes in a day. The system can automatically determine the user's stride length from the three-dimensional model. The system can track the user's location throughout a day in order to determine a distance the user walked throughout the day. The system can divide the distance by the user's stride length in order to determine the number of steps.

Figure 4C:
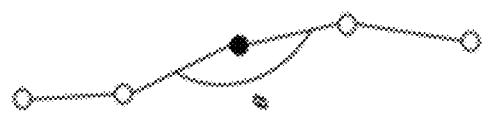
FIG. 4C illustrates a range of motion associated with the three-dimensional model of FIG. 4B during a shoulder raise exercise.
Figure 4B:
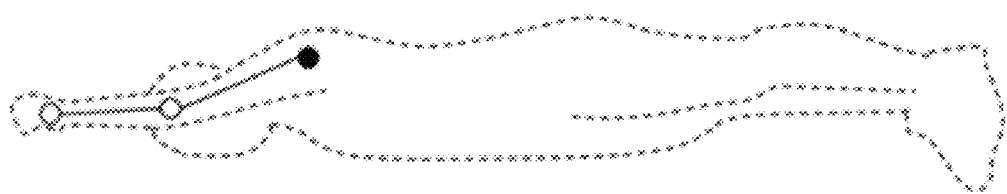
FIGS. 4A and 4B illustrate an example of a three-dimensional model during a shoulder raise exercise.
Figure 4A:
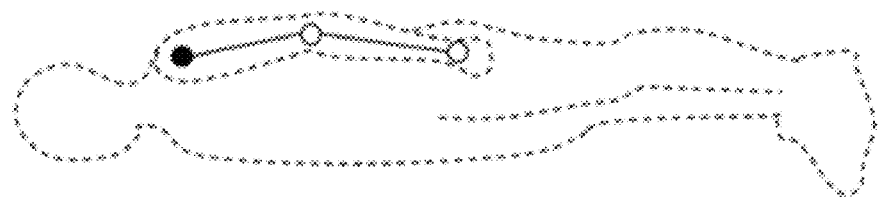

In some embodiments, the user's progress can be measured over time. For example, FIGS. 4A-4B show a user doing an arm raise. The starting position (FIG. 4A) and ending position (FIG. 4B) can change over time as the user's shoulder becomes stronger and/or more flexible. FIG. 4C shows a range of motion between the starting position of the upper arm and the ending position of the upper arm. This range of motion can be tracked over time to show progress, or a lack thereof. By creating a log of the user's completed physical therapy and their associated progress, a PT/trainer can understand the user's progress better. In some embodiments, the PT/trainer can view the progress intermittently and can make updates to the exercise program based on what they see. Furthermore, if the user reaches the end of their program and insufficient progress has been made despite exercise compliance, the data tracking log can be used to justify a new prescription for additional physical therapy. The data-based healthcare application of this concept can improve user outcome.

Figure 5A:
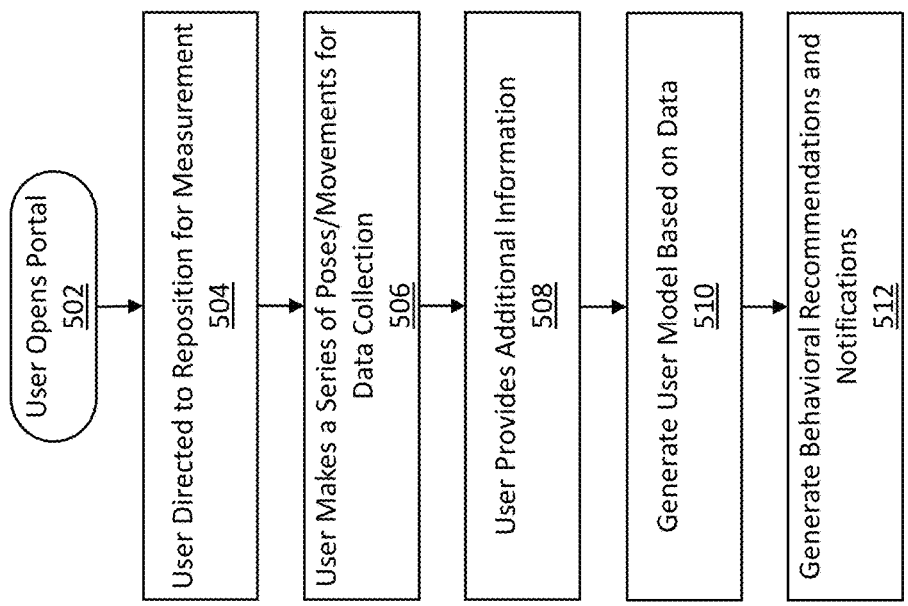
FIG. 5A illustrates a flow diagram of how a three-dimensional model of a user may be generated or updated.

FIG. 5A illustrates a flow diagram of how a 3D model of a user may be generated or updated.

At block 502 the user may access a portal (e.g., via an application or webpage) for performing image-based anthropometric measurements on their user device. In some embodiments, the user device may include various sensors such as a RGB camera, a depth and/or lidar sensor, and so forth; examples of user devices may include smartphones, tablets, laptops, desktop computers, etc. In some embodiments, the portal may be part of a standalone application or webpage. In other embodiments, the portal may be integrated with the telehealth proctoring platform described herein. For the sake of facilitating ease of understanding, this flow diagram may be understood within the example of a user accessing a mobile or web-based application on the user's smartphone to begin the measurement experience.

At block 504, the user may be directed (e.g., via the application or system) to reposition their body or move to a position where at least a portion of the body part to-be-measured (e.g., the user's lower body, upper body, full body) is visible by cameras and/or sensors of the user device. In some embodiments, the application may take photos of the user and determine whether a pre-selected portion or the whole body of the user is visible. If not, the system may instruct the user (visually and/or audibly) to move closer/further away and/or side to side. Once the user is in an acceptable position, the system may visually and/or audibly indicate to the user that their position is acceptable.

At block 506, the user may be directed to makes a series of poses or movements for data collection. For example, the user may be instructed to stand in a first pose (e.g., in standard anatomical position facing the user device or with arms lifted to the sides or any other position, etc.). The application may capture one or more images or measurements of the user in the first position using the cameras and/or sensors of the user device. The user may then be instructed to move to a second pose (e.g., rotated a first direction relative to the first pose), a third pose (e.g., rotated a second direction relative to the first pose), a fourth pose (e.g., with adjusted position such as standing with feet apart or arms lowered, etc.), such that each body region to be measured is imaged and captured from multiple angles. The pose selection and instruction by the system may be dependent upon which area of the body the user selects for measurement or may be generic to a full body measurement.

In some embodiments, the user may be instructed to make a series of movements and the application or system may capture a series of data sets (e.g., video and depth data) of the user performing the series of movements. For example, the system may instruct the user to start in a first pose (e.g., standard anatomical position) and to make at least one 360-degree revolution, such that the camera and/or sensors on the user device can substantially view and capture a full view of the user's body. A subset of the captured data/images can be selected by the system for further processing as key poses are identified (e.g., forward facing, 90-degree CCW, 180-degree, 90-degree CW, multiple images around each key pose, etc.). In some embodiments, additional data/images can be captured by the system (e.g., with long axis of an arm or leg pointing straight toward the camera/sensor) to improve system visibility of the user and measurement accuracy for certain areas of the body.

At block 508, the user may provide any additional information needed by the system that is useful in generating a 3D model of the user but was not directly obtained or collected via the camera/sensors. For example, the user may also input other health information such as weight, body fat percentage, food logs, exercise logs, sleep habits, heart rate, blood pressure, or other health metrics. In some embodiments, this step may be optional.

At block 510, the system may generate a 3D user model based on the collected data. In some embodiments, this user model generation may be done on the backend, and the application may send the collected/images data to the backend to generate the user model. In other embodiments, the user model generation may be done on the user's device. Thus, once the system has collected user data/images, the data/images may be processed to create a 3D user model. This 3D user model may be associated with the data/images collected from a particular imaging session, which reflect the user's body at the particular point in time that the imaging session was conducted.

In some embodiments, the user model may resemble the user models depicted in FIGS. 1A and 1B, and it may include an approximate user skeleton 102 that identifies the location of the user's joints 104 or other anatomical markers (e.g., a shoulder, an elbow, a wrist on a user's right arm or approximate ASIS locations of a pelvis) and creates line segments 106 in between. The user skeleton may or may not be substantially the same as an anatomic skeleton. For example, in some cases, the user skeleton may be based on a user's motion rather than their exact anatomic bone structure. The user skeleton may be mapped onto each data set/image of the subset of images selected for processing or may be mapped onto a 3D user model 108 created from the processed data sets/images (see FIGS. 1A, 1B). The 3D model may represent the user's body (e.g., contours, proportions, measurements, etc.) at the time of data collection. The 3D model may be a generic 3D volume or it may include images from an RGB camera on the user device fitted to 3D volume, such that the 3D model looks like the user. Additional images may be captured (e.g., a close-up image of the user's face) to improve realism. In some embodiments, the 3D model may be stored in a database and associated with the user and/or the time the 3D model was generated.

In this manner, a 3D model can be initially generated for the user (e.g., no previously generated 3D model exists for the user), or a 3D model can be generated for the user that corresponds to the instance in time the measurements occurred (e.g., an updated 3D model for the user). The same user skeleton may be applied over 3D models created at different times or updated user skeletons may be generated at each data collection session. The user skeleton should not change significantly over time even if the user's 3D model changes size. The locations where circumferential measurements are taken remain substantially the same between measurement events.

Thus, by completing additional data collection processes over time to create new 3D models, the user may be able to track measurement changes over time. The system may be able to compare the 3D models for the user in order to determine how specific measurements may have changed over time. In some embodiments, measurement events can be tracked over time and 3D models and/or measurement data can be displayed (numerically, graphically, etc.) to the user (e.g., via the application). This may help the user visualize body change over time to improve motivation and help keep the user on track with their goals.

At block 512, based on the 3D model, the system may generate behavioral recommendations and notifications that can be sent to the user in order to improve the user's health. In some embodiments, these recommendations and notifications may be sent to the user's device or provided to the user within an application. For example, the system may provide behavioral recommendations based on the generated 3D model, information input by the user, user goals, and/or accepted medical thresholds (e.g., target BMI thresholds, waist circumferences, etc.). The recommendations may include nutrition information and/or exercise information. In some embodiments, the system may provide an option for the user to connect with a healthcare provider to have more detailed discussions. In some embodiments, the system may send notifications or alarms to the user device to remind the user about exercise routines, to remind the user about nutritional goals, or to send intermittent messages of encouragement or congratulations when targets are achieved.

In some embodiments, the user may allow the system to access geolocation data associated with their user device to help with tracking steps, registering when the user enters a fitness center or grocery store, etc. Tailored notifications or suggestions associated with various locations may be enabled to provide reminders and improve motivation throughout the user's tracking experience. (e.g., "congratulations on reaching 10,000 steps today!" after achieving step goal; "Gym check-in complete!" when location at a fitness center detected; "Consider picking up ingredients for this easy, nutritional recipe!" when location at grocery store detected, etc.). In some embodiments, the system may even be able to estimate the distance the user has traveled based on measurements associated with the user's 3D model (e.g., if the user walks 10,000 steps, the length of the user's legs and their stride can be used to estimate total distance walked).

It should be noted that blocks 504, 506, and 506 in the figure may be collectively performed in a single session (e.g., an imaging session) to collect data/images of the user through the user device. The data/images can then be used in order to generate a 3D model or anthropometric measurements. Thus, an imaging session may be associated with the data/images of the user that were collected at a particular point in time and a 3D model or anthropometric measurements corresponding to the user's body at that point in time. Multiple imagine sessions may be conducted over a period of time for the user, which would allow for tracking the user's body over time (and the generation of 3D models/ anthropometric measurements that correspond to different points in time).

Figure 5B:
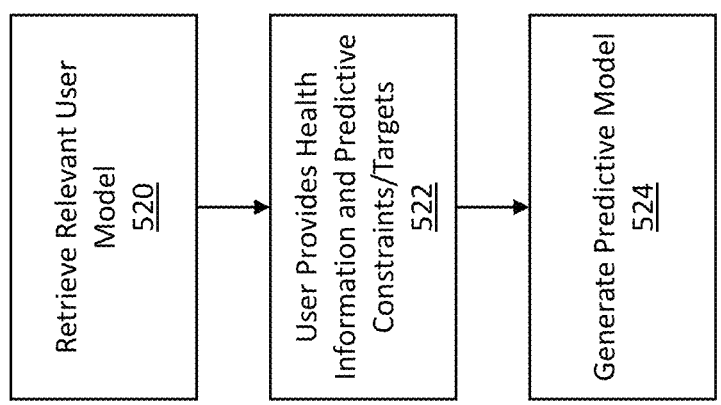
FIG. 5B illustrates a flow diagram of how a predictive three-dimensional model of a user may be generated.

FIG. 5B illustrates a flow diagram of how a predictive 3D model of a user may be generated.

At block 520, the system may retrieve a relevant 3D model for the user. For example, 3D models for a user may be stored in a database and each model may be associated with a time that user data for that model was taken, and the system may select and retrieve the most-recent 3D model for the user as a relevant 3D model for generating a predictive model.

At block 522, the user may provide additional health information that may not be determined from the 3D model (e.g., weight, body fat percentage, food logs, exercise logs, sleep habits, heart rate, blood pressure, or other health metrics), such as by entering this information into an application on their user device. The user may also enter predictive constraints or targets associated with the predictive model. For example, the user may input desired targets such as specific body part measurements and/or overall body composition targets (e.g., body fat percentage, muscle percentage, overall weight, etc.).

At block 524, the system may generate a predictive 3D model of the user based on the information provided by the user. The predictive 3D model may project how the user may look (e.g., at a time in the future). In some embodiments, the predictive 3D model may be generated by modifying the relevant 3D model of the user to meet the input constraints/ targets. In some embodiments, the predictive 3D model may be provided and displayed to the user (e.g., in the application) to help the user visualize their goals, and the user may even be able to make further modifications to the predictive 3D model that can be viewed in real-time. For example, the user may be able to access a user interface (e.g., in the application) that displays the predictive 3D model and also includes various sliders to control circumference measurements at selected parts of the body. Interacting with those sliders may modify the display of the predictive 3D model directly within the user interface.

Telehealth Proctoring Platform

Obesity is linked to many medical conditions, such as heart disease, stroke, high blood pressure, diabetes, arthritis, sleep apnea, gout, and some forms of cancer. In some cases, patients may seek surgical intervention to address weight issues, such as gastric bypass surgery, liposuction, and so forth. However, surgical interventions can carry risk, can be prohibitively expensive, and often fail to address underlying issues that led to obesity and related conditions. In some cases, it may be possible to halt or slow the progression of weight-related illnesses through diet and exercise. In some cases, one or more medications can be prescribed to aid in weight loss. In some cases, symptoms can be reduced or even eliminated. While weight loss can play an important role in improving the health of patients, often patients are unsure how to proceed or may struggle to stick with a weight loss program.

It can be important to monitor patients while they are engaged in a medical weight loss program. For example, if a patient is not seeing the expected results, this may indicate that the patient isn't taking prescribed medications properly, isn't adhering to dietary requirements of the medical weight loss plan, and so forth. In some cases, rapid weight loss may indicate that the patient is taking too much of a medication, isn't receiving sufficient nutritional intake, and so forth. In some cases, a patient may be receiving treatment for weight-related conditions such as diabetes. It can be important to monitor the patient so that medications can be adjusted or eliminated as the patient's health improves. For example, a patient's blood glucose levels could become dangerously low if the patient is taking medication to reduce blood glucose, but the patient's diet has changed such that the medication should be reduced or eliminated.

Monitoring a patient engaged in a medical weight loss program can be difficult. For example, patients may have to travel to a medical office or laboratory for periodic check-ins or lab work. It can be difficult for patients to schedule such visits. For example, travel may be required, appointments may only be available at times that are inconvenient for the patient (e.g., during hours when the patient is working), and so forth. Medical professionals can face lost time as patients show up late or skip appointments. Check-ins may be less frequent if the patient has to travel to the medical office. In some cases, patients may adhere to the weight loss plan shortly before an appointment but may otherwise not follow the plan closely, which can complicate treatment.

In some embodiments, a telehealth proctoring platform may be used to provide a patient with virtually proctored checkups as part of a medical treatment plan, such as a weight loss treatment program.

Figure 6:
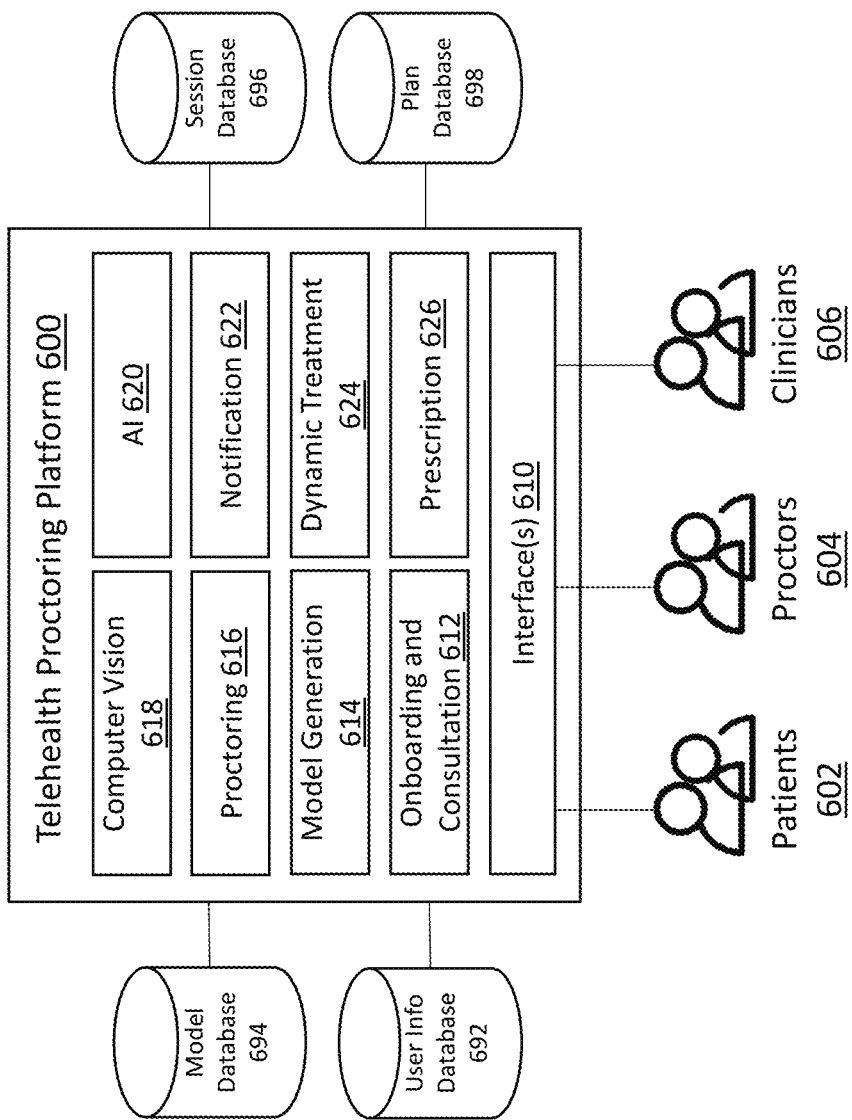
FIG. 6 illustrates a system diagram of a telehealth proctoring platform that can be used to proctor, monitor, and manage patients over the course of a medical treatment plan (e.g., a weight loss treatment program) by leveraging three-dimensional models and anthropometric measurements of the patients.

The telehealth proctoring platform may resemble the one shown in FIG. 6, which illustrates a system diagram of a telehealth proctoring platform 600 that can be used to proctor, monitor, and manage patients 602 over the course of a medical treatment plan (e.g., a weight loss treatment program) by leveraging three-dimensional models and anthropometric measurements of the patients 602.

It should be noted that functionality of the telehealth proctoring platform 600 may be shown as components, and that the various components of the telehealth proctoring platform 600 are illustrated and described in a manner to facilitate ease of understanding. In practice, one or more of the components may be optional, used together, or combined. Furthermore, one or more of the components may be separately located (e.g., with a third-party or at an endpoint) or their corresponding functionality may be performed at various locations. For example, generation and storage of a 3D user model for one of the patients 602 can be performed by an application running on the patient's user device (and that application may or may not be part of the telehealth proctoring platform 600), or alternatively, the generation and storage of a 3D user model for one of the patients 602 can be performed by a server on the backend.

Examples of the patients 602 may include any person receiving or registered to receive medical treatment as part of a medical treatment plan, such as a weight loss program. Examples of the proctors 604 may include medical professionals (e.g., physician, nutritionist, health coach, and/or the like) that can provide instructions or real-time guidance to a patient and monitor the patient's progress during the medical treatment plan. For instance, a proctor can be a medical professional that virtually meets with a patient to go over instructions for a medical weight loss program. Examples of the clinicians 606 may be any doctor that has contact with, and direct responsibility for, a patient and is capable of approving or modifying the patient's medical treatment plan.

The patients 602, proctors 604, and clinicians 606 may be able to interact with the telehealth proctoring platform 600 through one or more interfaces 610 associated with the telehealth proctoring platform 600. These interfaces 610 may include various user interfaces and/or application programming interfaces (APIs) depending on the implementation of the telehealth proctoring platform 600. For example, in some embodiments, one or more of the patients 602, proctors 604, and clinicians 606 may access the telehealth proctoring platform 600 via their user device by accessing an application installed on their user device or a web-based application, which will provide various user interfaces that can be interact with. In some embodiments, one or more of the patients 602, proctors 604, and clinicians 606 may access an application installed on their user device or a web-based application, and that application may communicate with the telehealth proctoring platform 600 via an API.

In some embodiments, the telehealth proctoring platform 600 may include an onboarding and consultation module 612 that is configured to collect information associated with the patients 602, proctors 604, and/or clinicians 606. In some embodiments, the information collected from the patients 602, proctors 604, and/or clinicians 606 may be stored in a user info database 692.

As an example, the onboarding and consultation module 612 may direct a patient new to the platform through an onboarding process to collect information about the patient, such as the patient's condition (e.g., what kind of medical treatment plan the patient is interested in), the patient's identifying information, the patient's health history, and so forth. In some embodiments, a patient may be able to sign up with the platform without a medical treatment plan already assigned to them (e.g., the patient may be looking to receive an initial consultation that could result in assignment of a medical treatment plan that is monitored through proctoring sessions on the telehealth proctoring platform 600).

In some embodiments, the onboarding may involve asking the patient a series of questions in a guided process to obtain the patient's biometric data and/or health data to determine the patient's eligibility for a particular pharmaceutical drug and/or medical treatment plan (e.g., drug treatment program). In some cases, such as for a medical weight loss program, the onboarding also may include the collection of data needed to generate a 3D model of the patient. For example, the patient may be asked to strike a set of poses that are captured by one or more cameras/sensors of their user device, and the images and sensor data may be sent back to the telehealth proctoring platform 600. In some embodiments, the platform may be able to use any patient data, including any associated biometric data about the patient (e.g., calculated anthropometric measurements) and/or the generated 3D model, in order to determine eligibility of the patient for a particular pharmaceutical drug and/or medical treatment plan.

In general, the telehealth proctoring platform 600 may be able to acquire patient data asynchronously or synchronously. For instance, to acquire patient data asynchronously, a patient can be asked a series of guided questions, and then the platform may direct the patient to use a device (e.g., a user device) with one or more cameras/sensors to acquire biometric data of the patient. As an example of acquiring patient data synchronously, a patient can be asked a series of guided questions while the platform simultaneously electronically communicates with other devices (having one or more cameras) to acquire biometric data of the patient.

In some embodiments, the telehealth proctoring platform 600 may include a model generation module 614 that is configured to generate 3D models for the patients 602. In some embodiments, generated 3D models for the patients 602 may be stored in a model database 694 for later reference and retrieval. All the 3D models generated for a particular patient may be associated with that patient and stored in the model database 694 for later retrieval. These 3D models may resemble the 3D models shown and discussed in connection with FIGS. 1A-4C, and the collection of information needed to generate the 3D models for the patients 602 may resemble the process shown and discussed in connection with FIG. 5A and FIG. 5B.

In some embodiments, the telehealth proctoring platform 600 may include a proctoring module 616 that is configured to establish a live, virtual proctoring session between a patient and a proctor. A patient may be assigned to a specific proctor or a group of proctors in advance (e.g., to a particular medical professional or group of medical professionals), or the patient may be assigned to one of the proctors 604 based on availability (e.g., who is available when the patient initiates a proctoring session), and/or based on personal considerations (e.g., the patient's sex, gender, age, co-morbidities, dietary preferences, and so forth). In some cases, a proctoring session may be an initial proctoring session for a patient seeking an initial consultation to determine the patient's eligibility for a particular medical treatment plan, while in other cases, a proctoring session may be for a patient already assigned a medical treatment plan.

Virtual proctoring sessions may be scheduled (e.g., at regular intervals as part of a medical treatment plan) or initiated by the patient on-demand. For example, proctoring sessions may be scheduled as a periodic check-in (e.g., between a patient and one or more medical professionals) that the patient may have to attend in order to comply with a medical treatment plan such as a weight loss program. The proctoring session can be used to collect check-in data from the patient, monitor the patient during an exercise or procedure, and confirm continued adherence to the medical treatment plan. Alternatively, proctoring sessions may be initiated by a patient on-demand or with short notice (e.g., a same-day appointment, an appointment within a few days, and so forth) for a variety of reasons, such as to seek clarification/guidance or to review the medical treatment plan with a medical professional.

The flexibility (e.g., remote, scheduled or on-demand, and seamlessly managed by the telehealth proctoring platform 600) of the virtual proctoring sessions and the manner that they are implemented in the telehealth proctoring platform 600 (e.g., allowing for collection of data and anthropometric measurements, the tracking of patient data over time, etc.) may provide numerous benefits, and a non-inclusive list is provided. First, they allow the telehealth proctoring platform 600 to enable greater interaction between the patient and a medical professional. For example, in the context of a weight loss program, a patient may have a question about a dietary plan, about their medication, about food substitutions, and so forth, and the patient can connect to a medical professional to inquire. As another example, a patient may be planning a vacation or trip and can conveniently use the telehealth proctoring platform 600 to inquire about strategies for eating healthily while away from home. Second, the virtual proctoring sessions are remote and less burdensome, so they can be used for periodic check-ins on a more frequent basis, which can enable medical professionals to identify compliance issues earlier and also identify issues that would otherwise go unnoticed. Third, the virtual proctoring sessions can be used to easily track patient compliance with a medical treatment plan by monitoring or tracking a patient's self-administration of an exercise, procedure, treatment, or medication. For example, in the context of a weight loss treatment program, the virtual proctoring sessions can be used to monitor the patient during self-administration of pharmaceutical drugs associated with weight loss. If the patient skips a drug dosage and/or administers too high/low of a dosage, then the platform may determine that the patient is no longer in compliance with the weight loss treatment program. Fourth, on-demand virtual proctoring sessions may actually improve patient compliance with medical treatment plans. For example, in the case of weight loss treatment programs, patients often fail to comply for a variety of reasons that include confusion, lack of motivation, difficult obtaining healthy food, inability to afford healthy food or medication, and so forth. Thus, a patient could initiate an on-demand virtual proctoring session in order to clear up some confusion they might have or to obtain guidance, thereby increasing the chances of the patient's compliance with the medical treatment plan.

Thus, within the context of a weight loss treatment program, a virtual proctoring session can be used as a check-in to provide motivation to a patient who is struggling to adhere to the weight loss program. For example, a proctor can review weight loss progress with the patient. In some embodiments, the proctor can use charts or numerical data to help the patient understand progress that has been made. For example, the proctor can discuss an amount of weight lost, improvements in one or more lab numbers (e.g., cholesterol levels, blood pressure, blood glucose), and so forth.

In some embodiments, recordings (e.g., video recordings) associated with a proctoring session may be saved in a database such as a session database 696, and data associated with a proctoring session may also be saved in the session database 696 or saved in the user info database 692 for the patient. In some embodiments, proctoring sessions may additionally be used to collect various measurements or biometrics associated with a patient's body in order to track patient progress and compliance. For example, one or more cameras on the patient's user device can be to obtain various measurements of a patient's body to observe and/or report weight loss brought on by a weight loss program being administered to the patient. The platform may be able to capture anthropometric measurements as disclosed herein, which can be used to obtain measurements of various body areas and calculate/generate weigh loss data.

In some embodiments, an anthropomorphically correct 3D model for the patient may be generated (e.g., by the model generation module 614) or retrieved (e.g., from the model database 694) in association with a virtual proctoring session between a patient and a proctor. In some embodiments, a 3D model for the user may be viewed, or interacted with, by the patient/proctor during the proctoring session. For example, the 3D model can be used to help the patient to visualize weight loss. The proctor may be able to use the 3D model to show the patient a starting point and how the patient appears now. In some embodiments, the telehealth proctoring platform 600 can be configured to generate (e.g., via the model generation module 614) a predictive 3D model representation of how the patient will appear in the future—for example—in one week, in one month, at the conclusion of the medical weight loss program, and so forth.

In some embodiments, the telehealth proctoring platform 600 may include a computer vision module 618. The computer vision module 618 may utilize various image processing techniques and/or computer vision techniques to analyze the video conferencing feed, video recording, and/or still images captured from a proctoring session (either in realtime or on historical data, e.g., saved to session database 696). In some embodiments, the computer vision module 618 may perform this analysis with the AI module 620 or by utilizing various AI and/or machine learning techniques.

In some embodiments, from a proctoring session, the computer vision module 618 may be able to identify or determine the drug dosage being administered to a patient and/or whether a patient is incorrectly administering a drug dosage, thereby causing the patient to get too much or too little of the pharmaceutical drug. In some embodiments, from the proctoring session in which the patient injects a needle into their body, the computer vision module 618 may be able to determine whether the needle entered the patient's body at the correct depth, angle, period, time, or the like— thereby ensuring that the patient is conducting the procedure correctly and/or that the patient is compliant with the medical treatment plan. In some embodiments, the information obtained from the computer vision module 618 may be used to generate and send an electronic alert to one or more users of the platform (e.g., a patient, proctor, clinician, administrator, doctor, nurse, etc.). For instance, the electronic alert may notify the user that the patient was administered the incorrect drug dosage, conducted the procedure incorrectly, or is noncompliant with the medical treatment plan. In some embodiments, this electronic alert may even be sent to the proctor while the proctoring session is still ongoing, thus quickly bringing the issue to the attention of the proctor. In some embodiments, this alert may be generated by the notification module 622.

In some embodiments, the telehealth proctoring platform 600 may include an AI module 620. The AI module 620 may include one or more artificial intelligence systems that use any number of algorithms or techniques (such as machine learning algorithms, rules, heuristics, etc.) to make predictions or determinations for the telehealth proctoring platform 600.

For example, in some embodiments, the AI module 620 may include an artificial intelligence system that predicts future weight loss/gain of a patient and/or the predicted weight of a patient based in part on one or more of the following: historical weight loss data, historical patient data, drug treatment plan data, drug type data, historical population data, trajectory data for the patient, patient biometric data, patient health data, proctor monitoring data of the patient utilizing the drug therapies, and the like (e.g., "patient data"). In some embodiments, the artificial intelligence system may be able to use the predicted future weight loss/gain of a patient and/or the predicted weight of a patient in order to dynamically adjust the patient's treatment plan (either directly, or through the dynamic treatment module 624). For example, the platform may be used to monitor and observe a patient under a weight loss treatment plan, and it is determined that the patient is losing weight too rapidly determined or the patient is predicted to lose weight too rapidly. The platform may then dynamically adjust the drug dosage (e.g., lower the dosage) for the particular pharmaceutical being administered to the patient under the weight loss treatment plan.

In some embodiments, the AI module 620 may include an artificial intelligence system that can dynamically determine if a patient is eligible to take a particular pharmaceutical drug, a drug treatment program, and/or medical treatment plan based on a patient's biometric and/or health data as inputs. In some embodiments, the AI module 620 may include an artificial intelligence system that can utilize the patient biometric data received from a plurality of patients in order to analyze the efficacy of different treatment plans and/or different pharmaceutical drugs. In some embodiments, the AI module 620 may include an artificial intelligence system that can dynamically generate predictions regarding whether a particular pharmaceutical drug is more likely to be efficacious for a particular patient with a particular biometric makeup. In some embodiments, the AI module 620 may include an artificial intelligence system that can determine and select a particular pharmaceutical drug that is predicted to be highly efficacious for a particular patient having a particular biometric makeup. In some embodiments, the artificial intelligence system may be able to dynamically generate a patient specific dosing regimen for the particular pharmaceutical drug that is predicted to be particularly efficacious for the particular patient. In some embodiments, the artificial intelligence system may be configured to determine and select a particular pharmaceutical drug, based in part on the predicted efficacy of the pharmaceutical drug on a particular patient and/or based on the patient's economic ability to obtain and/or pay for the selected pharmaceutical drug. In some embodiments, the selected drug and dosing regimen may be used in the generation of a medical treatment plan for the patient (e.g., by the dynamic treatment module 624).

In some embodiments, the AI module 620 may include an artificial intelligence system configured to act as a safety mechanism for tracking (in real time or substantially real time) the health of the patient while the patient is being administered pharmaceuticals, such as drugs configured to produce weight loss, in order to ensure the health of the patient. For example, the artificial intelligence system can be configured to analyze patient data in order to identify patient safety issues, which can trigger the platform to generate an electronic alert (e.g., via the notification module 622) to the patient, platform administrator, physician, nurse, physician aid, or other user of the platform.

In some embodiments, the AI module 620 may include an artificial intelligence system that can utilize biometric data collected from a plurality of patients in order to manage and/or predict supply chain issues relating to pharmaceutical drugs to be administered in medical treatment plan. For example, the artificial intelligence system may be able to identify and/or predict, on a month by month basis (or other period basis), the amount of a particular pharmaceutical drug that is needed to service the patients within a population that rely on a medical treatment plan administered by the platform. In some cases, this information can be used (e.g., by the dynamic treatment module 624 and/or the prescription module 626) to alter the treatment plan and prescriptions for some of the patients (e.g., switch some patients from drug 'A' to drug 'B' to alleviate the supply chain issues). In some embodiments, the prediction data related to the required amount of a particular pharmaceutical drug for a particular period may be used to electronically order a supply of the pharmaceutical drug to satisfy the predicted demand.

In some embodiments, the AI module 620 may include an artificial intelligence system that is configured to additionally factor in economic/market data in order to select a prescription drug for a particular patient in connection with a medical treatment plan. For example, the artificial intelligence system may consider historical insurance data, patient historical data, industry market data, pricing data, drug efficacy data, patient biometric data, and the like, in order to select a suitable prescription drug for a particular patient in connection with a medical treatment plan. In some embodiments, the artificial intelligence system may be configured to utilize historical pricing data of a first drug and a second drug, and/or drug supply data at a particular pharmacy selected by the patient for the first and second drugs, and/or drug efficacy of the first and second drugs, in order to dynamically select between the first and second drugs. In some embodiments, an electronic physician's prescription notice may be automatically generated (e.g., by the prescription module 626) based on the selected drug.

In some embodiments, the telehealth proctoring platform 600 may include a notification module 622 for generating and sending out various messages, communications, alerts, notifications, and reports to the various users of the telehealth proctoring platform 600 for various purposes. For example, various electronic alerts or messages (e.g., visual message, text based message, audio based message, text to speech message, alert sound, or the like) may be sent through an electronic network, such as the Internet or a cellular network, for display on a user device (e.g., a mobile device, computer, mobile phone).

In some embodiments, the platform may send messages to participants of a virtual proctoring session in the form of a text message, an instant message, a pop-up message, a web screen message, or the like. In some embodiments, the platform may generate and send messages (e.g., video messages) to a patient that demonstrate or instruct on how to adjust the drug dosage for a treatment plan, such as by adjusting a medical device utilized to administer the drug (e.g., an injection pen device). The notification module 622 may be able to generate these messages to incorporate and reflect updates to the patient's treatment plan. Thus, when a patient's treatment plan is dynamically adjusted (e.g., via the AI module 620 or the dynamic treatment module 624), such as with a new dosage, the notification module 622 may generate and send an electronic message to the patient with specific instructions for the patient to adjust the amount of pharmaceuticals to be administered to the updated dosage.

In some embodiments, the notification module 622 may be able to generate and send electronic alerts to the patient, proctor, clinician, physician, nurse, administrator, or any other user of the platform based on compliance data collected by the platform. For example, the platform may send an electronic message that alerts the patient is noncompliant with a medical treatment plan, an electronic message that recommended steps for getting the patient back in compliance with the medical treatment plan, an electronic message detailing a revised treatment plan, and so forth.

In some embodiments, the notification module 622 may enable the platform to generate an electronic report based on biometric data from a plurality of patients and then electronically transmit the report to a government entity, a quasi-government entity, or any other entity for compliance/research purposes. In some embodiments, the electronic report may be anonymized, and patient identification information may be removed before the report is electronically transmitted.

In some embodiments, the telehealth proctoring platform 600 may include a dynamic treatment module 624 that allows for dynamic adjustment and modification of a patient's medical treatment plan in order to improve outcomes, meet specific goals, or avoid harm to the patient. In some embodiments, the various medical treatment plans (including updated treatment plans) associated with a patient may be stored in a database such as a plan database 696, allowing for the most up-to-date treatment plan for a patient to be retrieved and referenced in order to determine compliance. In some embodiments, the platform may display or electronically transmit a generated treatment plan to a clinician or other physician for approval. In some embodiments, the clinician may be able to provide approval for a proposed treatment plan or be able to make additional modifications to a proposed treatment plan or the patient's existing treatment plan, and the finalized treatment plan may be saved to the plan database 696.

In some embodiments, the dynamic treatment module 624 may generate or adjust a treatment plan based on goals or inputs provided by the patient. For example, within the context of a weight loss treatment plan, a patient may provide input (e.g., during the onboarding/consultation process or via sliders associated with a 3D model) regarding their desired weight loss or other comparable patient outcome, and the dynamic treatment module 624 may generate a proposed treatment plan enabling the patient to obtain that outcome.

In some embodiments, the dynamic treatment module 624 may generate or adjust a treatment plan based on observed or predicted trends in data associated with a patient (e.g., the predicted future weight loss and/or weight gain and/or predicted weight of the patient), such as by adjusting the drug dosage for a particular pharmaceutical being administered to the patient in accordance with the weight loss treatment plan. For example, if the patient is making rapid weight loss progress, then the patient's treatment plan could be updated with a lowered drug dosage. In some cases, the updated treatment plan could be sent to a clinician for review and approval.

In some embodiments, the dynamic treatment module 624 may generate or adjust a treatment plan to incorporate a remediation action that is designed to remedy an incorrect administration of drug dosage to the patient or fix issues associated with noncompliance with a treatment plan. For example, if the patient was injected with too high/low of a drug dosage, then for the next dose the patient may be injected with can be at a dynamically prescribed dosing level (e.g., lower/higher) to compensate.

Examples of how a medical treatment plan may be structured or laid out, or examples of the information contained in a medical treatment plan, can be seen in FIGS. 7A-7C of U.S. Provisional Patent Application No. 63/491,701, entitled "SYSTEMS, METHODS, AND DEVICES FOR VIRTUALLY SUPERVISED MEDICAL WEIGHT LOSS TREATMENT PROGRAM ADMINISTERED VIA ON DEMAND TELEHEALTH PROCTOR-OBSERVED PLATFORM," which was previously incorporated by reference in its entirety.

In some embodiments, the telehealth proctoring platform 600 may include a prescription module 626. The prescription module 626 may dynamically generate an electronic physician's prescription notice based on a clinician's approval and/or a proposed treatment plan. The proposed treatment plan can be a modified treatment plan or a dynamically generated treatment plan. In any of the instances disclosed herein, wherein the treatment plan is altered dynamically by the system, then the systems disclosed herein can be configured to dynamically adjust a physician prescription to account for the changes in the treatment plan, for example, the system can be configured to dynamically and automatically generate an electronic physician prescription wherein the amount of drugs being order from the pharmacy is increased or reduced depending on the changes to the treatment plan. The electronic physician's prescription notice may be electronically transmitted to a pharmacy so that the patient can obtain the prescribed pharmaceutical drugs for use with the proposed treatment plan.

In some embodiments, the telehealth proctoring platform 600 may be able to dynamically send an electronic alert or message (e.g., via the notification module 622) to a delivery service or entity (for example Uber, Lyft, Instacart, or the like). The electronic alert or message may provide a delivery person with information about where to pick up the prescribed pharmaceutical drugs (e.g., at the specifically designated pharmacy) and where to deliver the drugs (e.g., to the patient).

In some embodiments, the prescription module 626 may be configured to dynamically generate a release code, bar code, QR code, or the like that enables the delivery person to pick up the pharmaceutical drugs at the designated pharmacy. For example, the dynamically generated release code, bar code, QR code, or the like acts as a release authorization required to pick up the pharmaceutical drugs at the specified pharmacy on behalf of the patient. In some embodiments, the the pharmacy may be allowed to scan the release code, bar code, QR code, or the like to identify what pharmaceutical drugs are to be provided to the delivery person, and to verify that the pharmaceutical drugs should be released to the requesting delivery person. In some embodiments, the delivery person may be prompted to provide identification to verify that the delivery person is authorized to receive the pharmaceutical drugs on behalf of the patient. In some embodiments, the systems disclosed herein can be configured to dynamically generate mapping instructions for delivering the pharmaceutical drugs to the patient. In some embodiments, the mapping instructions may be generated based on receiving an electronic message from the pharmacy that the pharmaceutical drugs have been picked up by the delivery person.

In some embodiments, the prescription module 626 may be configured to dynamically track the route movement of the delivery person as the delivery person travels from the pharmacy to the patient's location. In some embodiments, the platform may electronically display to the patient in real time or substantially real time the tracked route movement of the delivery person, such that the patient can track the delivery status of the pharmaceutical drugs to the patient. In some embodiments, the prescription module 626 may be configured to electronically transmit the electronically generated physician's prescription notice to an insurance company system in order to obtain prior authorization for the administration of the prescribed pharmaceutical drugs.

In some embodiments, the prescription module 626 may be configured to electronically receive an electronic message from an insurance company system, wherein the electronic message indicates whether the patient is covered under insurance for use of the prescribed pharmaceutical drugs. In some embodiments, the prescription module 626 may be able to utilize the electronic message from the insurance company system to dynamically generate a modification of the physician's prescription notice or a new physician's prescription notice directed to a second pharmaceutical drug. In some embodiments, the prescription module 626 may be configured to dynamically resubmit the new physician's prescription notice to determine whether the second pharmaceutical drug is approved by the insurance company of the patient.

In some embodiments, the platform may be able to apply an artificial intelligence system (e.g., via the AI module 620) to historical insurance data, patient historical data, industry market data, pricing data, drug efficacy data, patient biometric data, and the like, to dynamically select a prescription drug for a particular patient in connection with a particular drug treatment plan. For example, in some embodiments, the systems disclosed herein can be configured to utilize historical pricing data of a first drug and a second drug, and/or drug supply data at a particular pharmacy selected by the patient for the first and second drugs, and/or drug efficacy of the first and second drugs in order to dynamically select between the first and second drugs, and then dynamically generate (e.g., via the prescription module 626) an electronic physician's prescription notice based on the selected drug.

In some embodiments, the systems disclosed herein can be configured to manage the reimbursement payments made by the insurance company and/or a health savings account (HSA) in connection with the patient's purchase of the prescribed drugs. In some embodiments, the systems disclosed herein can be configured to receive patient biometric data over time from a plurality of patients that the platform is monitoring, observing, and reporting on via the proctoring features of the platform.

Thus, it can be understood that the telehealth proctoring platform 600 described herein can offer many advantages. For example, the patients 602 may not need to travel for periodic check-ins. In some embodiments, the patients 602 can speak with proctors 604, clinicians 606, or other medical professionals (e.g., physician, nutritionist, health coach, and/or the like) on demand or with short notice (for example, a same-day appointment, an appointment within a few days, and so forth).

In some embodiments, the telehealth proctoring platform 600 can be used to enable proctors 604, clinicians 606, or other medical professionals (e.g., physician, nutritionist, health coach, and/or the like) to provide instructions to a patient, such as instructions for a medical weight loss program. In some embodiments, the patients 602 may be able to conduct some forms of testing at home under proctored supervision, such as checking blood glucose levels. In some embodiments, the patients 602 may be able to provide anthropometric measurements of their bodies by capturing images of themselves in various poses during an imaging session while under proctored supervision. Patient data collected under proctored supervision may be more accurate and reliable and can be used to monitor/track a patient's body over time.

Figure 7:
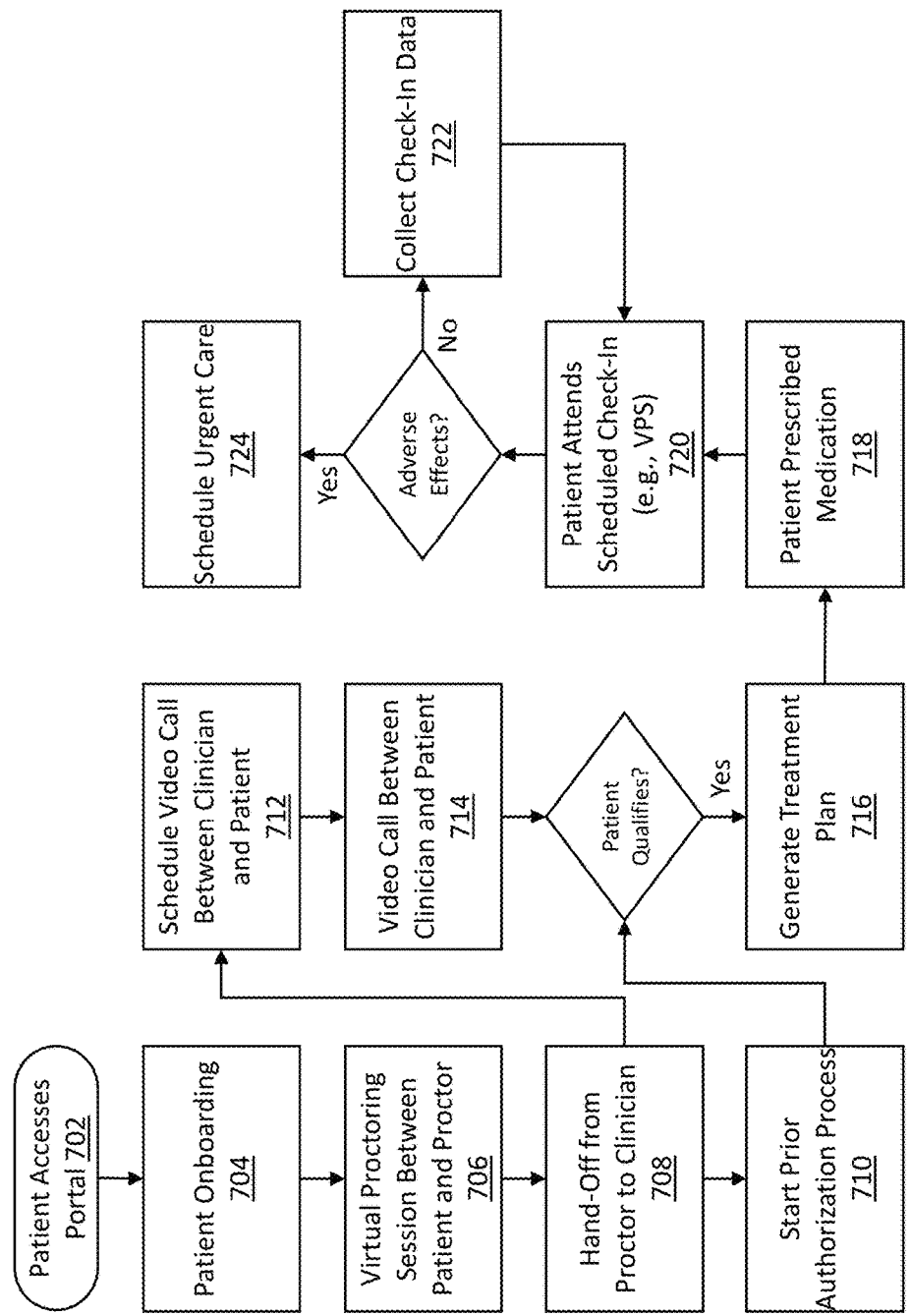
FIG. 7 illustrates an example process flow for determining patient eligibility for a medical treatment plan and monitoring the patient's adherence to the medical treatment plan over time, which can be used with embodiments of the telehealth proctoring platform described herein.

FIG. 7 illustrates an example process flow for determining patient eligibility for a medical treatment plan and monitoring the patient's adherence to the medical treatment plan over time, which can be used with embodiments of the telehealth proctoring platform described herein.

At block 702, a patient may access a portal, such as a portal on a website or through an application on their user device, associated with a telehealth proctoring platform. The patient may select among various options to choose a subscription plan or an option associated with what the patient is looking to obtain a consultation for (e.g., medical treatment plan for weight loss). In some embodiments, the patient may have to provide payment or payment information upfront and go through a checkout procedure to purchase the selected option. In some embodiments, once the patient completes the checkout procedure, the platform may send the patient an email with their order confirmation, any further instructions, and/or a link to proceed with their consultation. In some embodiments, the patient may be directed to a checkout landing page with a link to begin the onboarding process. In some of such embodiments, there may be a button to start onboarding, and the button may have a delayed start (e.g., there may be a 15 second pause before the patient can access the onboarding feature).

At block 704, the patient may choose to start the onboarding process, which may involve the patient setting up a login and password with the platform. In some embodiments, the patient's account may be already created, and the patient furnishes a one-time login and/or password. The patient may be presented with a number of screening questions associated with the treatment/condition that the patient previously expressed interest in (e.g., medical treatment plan for weight loss). These screening questions may serve as a first step towards filtering out patients that would be unsuitable for a medical treatment plan offered by the system. Thus, if the patient provides answers to the screening questions that reveal the patient to be a poor fit, the patient may be notified by the system that they are ineligible and will be provided a refund. In some embodiments, a customer service representative may reach out to the patient to initiate the refund process (e.g., via chat, e-mail, mobile messaging, SMS, and so forth). However, if the patient is eligible, then the patient may be directed to answer additional clinical intake questions or provide additional information that may be useful in assessing the patient.

At block 706, the patient may enter a live, virtual proctoring session with a proctor over the telehealth proctoring platform. In some embodiments, the patient's user device captures a live video stream of the patient that is provided to the proctor. During the proctoring session, the proctor may verify the patient's identity, such as by inspecting identification provided by the patient (e.g., the patient holds their driver's license or other suitable user ID up to the camera of their user device so that the proctor can inspect it and compare it to the patient's face). The proctor may also verify insurance, such as by inspecting insurance cards or other insurance information provided by the patient. The proctor may also ask the patient additional questions to further determine whether the patient is eligible and suitable for the medical treatment plan.

At block 708, if the patient is determined to be suitable, then the proctor may initiate a process to hand off the patient to a clinician. In some embodiments, this may involve the proctor informing the patient of the clinician schedules or hours of availability for conducting video calls. In some embodiments, the clinicians may be onboarded with the telehealth proctoring platform directly, and the platform can seamlessly handle the assigning, scheduling, and conducting of video calls with clinicians (e.g., blocks 710/712/714) without a third-party.

In other embodiments, a third-party system or platform (e.g., OpenLoop's telehealth platform) may take over to handle the patient's consultation with a clinician, including scheduling video calls with the clinician. In such cases, the proctor may create a profile for the patient in order to transfer the patient over to the third-party system.

In some embodiments, this may start the eligibility and benefits (E&B) verification process. An estimate can be obtained after a short period of time (e.g., under two hours) and a copay invoice can be submitted to a payment processor or payment processing system, which may send an email to the patient regarding copay. In some embodiments, the telehealth proctoring platform or the third-party system may email the patient with an explanation of benefits. At block 710, the third-party system may initiate a prior authorization process with the patient's health insurance company. The health insurance company may review the medical treatment plan or medication that the patient is consulting for and determine its necessity in treating the patient's condition. A successful review resulting in prior approval may indicate that health insurance plan plans to cover the medical treatment plan.

At block 712, a video call may be scheduled between a clinician and the patient. For example, in some embodiments, a third-party system may add the patient to a queue for conducting a video call with a clinician. If it is currently outside the schedules or hours of availability for the clinicians, the patient may be added to a priority queue for conducting a video call during the next available shift for the clinicians. Otherwise, the patient may be contacted or informed of clinician availability and provided details for attending the video call (e.g., the patient may be texted a link to join the video call with the clinician). However, if the patient is unavailable to attend the video call, then the video call may be rescheduled for a more convenient time or the patient may be provided a refund, with a customer service representative reaching out to the patient to initiate the refund process.

At block 714, a video call can take place between the patient and the assigned clinician. During this video call, the clinician may converse with the patient to assess the patient's fit for the medical treatment plan. The clinician may also order lab tests if needed. Following the call, if it is determined that the patient is not a good fit for the medical treatment plan, then the refund process may be initiated with a customer service representative reaching out to the patient to discuss the refund process. However, if the patient qualifies for the medical treatment plan (e.g., the patient is a good fit and/or the prior authorization is approved), then at block 716, an initial medical treatment plan tailored to the patient may be generated. This tailored medical treatment plan may be modeled off a default plan, modified by the clinician, or dynamically generated by an artificial intelligence system in the telehealth proctoring platform (e.g., AI module 620 in FIG. 6). It may be based on various factors such as the patient's health history or desired outcome (e.g., increase a drug dosage if the patient has a desired outcome that is more aggressive).

At block 718, the user may be prescribed medication in accordance with the medical treatment plan. In some embodiments, the telehealth proctoring platform may be able to generate an electronic prescription and submit it to a pharmacy of the patient's choosing. The patient may be notified, such as via e-mail or text, that the prescription was successfully sent to the pharmacy. The patient may also be provided with instructions for attending testing or check-ins that are regularly scheduled based on the treatment plan, such as weekly testing or check-ins.

At block 720, the patient may attend a virtual proctoring session via the telehealth proctoring platform for any scheduled testing or check-in. In some embodiments, if a patient misses a session (e.g., the patient is X days overdue for a session), then the platform may remind the patient to start their weekly treatment, such as via email or SMS.

As previously discussed, each virtual proctoring session may be between the patient and a proctor. During the proctoring session, the proctor may verify the patient's identity and monitor/observe the patient as they self-administer treatment (e.g., an injection procedure) or medication, carry out a diagnostic test, perform an exercise or procedure, and so forth. The proctor may ask the patient various questions, such as if the patient has experienced adverse effects in association with the treatment plan. If the patient has not experienced any adverse effects, then the check-in session may conclude with block 722 and the collection of any relevant data. For example, within the context of a weight loss program, the patient's weight could be collected (e.g., by having the patient stand on a scale and capturing a photo of the scale's readout). This data can be stored by the platform, reported to the patient's clinician, sent to third-party systems, and so forth. In some embodiments, the platform may also send a progress report to the patient containing a link to a user portal, such as via email or SMS.

However, if the patient has experienced adverse effects, then the platform may schedule an urgent care request for the patient at block 724. In some embodiments, a request for urgent care and consult by a clinician may be passed off to a third-party system. This process for scheduling a consult with a clinician may resemble the video call scheduling associated with block 712; the patient may be added to a high priority queue for calls with clinicians. If it is during the hours of availability for clinicians, then the patient may be contacted or informed of clinician availability, to confirm call scheduling, and provided details for attending the video call (e.g., the patient may be texted a link to join the video call with the clinician at the scheduled time). If it is outside the hours of availability for clinicians, then the video call may be rescheduled for a more convenient time or the patient may be added to a priority queue for conducting a video call during the next available clinician shift.

At-Home Tests and Diagnostics

As previously mentioned, it can be difficult to obtain accurate measurements or collect accurate data from a patient when a patient-performed procedure is involved because the patient may not be properly following procedures and protocol. One such example scenario may be when the patient is providing results of a self-administered (e.g., at-home) test or diagnostic, since the patient may be reading the results incorrectly, not following proper test procedure or protocol, tampering with the test procedure, manipulating the results, and so forth.

In some embodiments, the telehealth proctoring platform described herein can be used to establish virtual proctoring sessions in order to collect accurate data from a patient when the data is associated with a self-administered test or diagnostic, such as at-home blood collection devices and/or other home diagnostic devices. The data collected under proctored supervision can be used by the platform like any other kind of patient data, such as to track changes to the patient's body over time, to dynamically generate a medical treatment plan, to select a particular medication prescribed to the patient, and so forth.

One specific example of an at-home blood collection or diagnostic device an A1C test for checking blood glucose levels. The A1C status is determined by a test that measures the amount of hemoglobin with attached glucose and reflects the patient's average blood glucose levels over the past 3 months. The A1C test result is reported as a percentage. The higher the percentage, the higher the blood glucose levels have been. A normal A1C level is below 5.7 percent.

In some embodiments, the telehealth proctoring platform can be used to have a patient self-administer an A1C test under remote proctor supervision and then show the test results in order to provide an accurate A1C level for the patient. The A1C level for the patient could be used to determine the patient's medical treatment plan (e.g., put the patient on a weight loss program if the blood glucose levels are too high) or to track the patient's A1C level over time.

Computer Vision-Assisted Exercise and Physical Therapy

The telehealth proctoring platform described herein may be used to ensure that a patient is following proper procedures and protocol, and it does not have to be in connection to a measurement or test. For instance, the telehealth proctoring platform can be used to promote compliance with exercise and physical therapy.

In some embodiments, a user may meet with a physical therapist or trainer (e.g., in person, over a video call, or a virtual proctoring session established by the telehealth proctoring platform). The PT/trainer can record a video the user doing a single repetition of each exercise while they are instructing the user how to do the exercise. This video can be provided to the platform later as a baseline against which all repetitions of the exercise can be compared. When the user is performing the exercise under the supervision of the platform, if the user's movement deviates from the baseline movement, the platform can detect this and notify the user or instruct the user on how to complete the motion correctly.

In some embodiments, the user can start a PT/exercise application on their user device/smartphone and can be instructed on how to position the user device for each exercise so that the exercise motion is viewable by the system. For example, on an arm raise, the system can instruct the user to position themselves such that the arm being raised is directly in front of the user device camera. The system can identify the joints, limbs, or body regions involved in the exercise and can generate the user skeleton associated with those joints, limbs, or body regions. The user skeleton is then tracked over the full range of motion of the exercise. Deviations can be noted for the user in real time or can be logged for the PT/trainer to view. Repetitions of the exercise can be counted (e.g., out loud for the user up to their assigned number of repetitions) or can be otherwise tracked in a log and checked off when complete. This can help the user with remembering to do their exercises and can help with compliance and rehabilitation.

In some embodiments, the telehealth proctoring platform and the generated 3D user models described herein can be used to help with exercise and physical therapy compliance. For example, when a patient is prescribed physical therapy as part of a medical treatment plan (or is partaking in an exercise program), specific details such as the exercises (and number of sets/repetitions) the patient must perform can be tied to the patient and the patient's treatment plan. For example, the patient can be prescribed to complete 2 sets of 10 arm raises.

In some embodiments, the user can start a PT/exercise application on their user device/smartphone and can be instructed on how to position the user device for each exercise so that the exercise motion is viewable by the system. For example, on an arm raise, the system can instruct the user to position themselves such that the arm being raised is directly in front of the user device camera. The system can identify the joints, limbs, or body regions involved in the exercise and can generate the user skeleton associated with those joints, limbs, or body regions. The user skeleton is then tracked over the full range of motion of the exercise. Deviations can be noted for the user in real time or can be logged for the PT/trainer to view. Repetitions of the exercise can be counted (e.g., out loud for the user up to their assigned number of repetitions) or can be otherwise tracked in a log and checked off when complete. This can help the user with remembering to do their exercises and can help with compliance and rehabilitation.

In some embodiments, the user's progress can be measured over time. In some of such embodiments, the 3D models generated for the user and/or the anthropomorphic measurements associated with them can be used to assist with determining this progress over time. For example, FIGS. 4A-4B show a user doing an arm raise. The starting position (FIG. 4A) and ending position (FIG. 4B) can change over time as the user's shoulder becomes stronger and/or more flexible. FIG. 4C shows a range of motion between the starting position of the upper arm and the ending position of the upper arm. This range of motion can be tracked over time to show progress, or a lack thereof. By creating a log of the user's completed physical therapy and their associated progress, a PT/trainer can understand the user's progress better. In some embodiments, the PT/trainer can view the progress intermittently and can make updates to the exercise program based on what they see. Furthermore, if the user reaches the end of their program and insufficient progress has been made despite exercise compliance, the data tracking log can be used to justify a new prescription for additional physical therapy. The data-based healthcare application of this concept can improve user outcome.

Computer Systems

Figure 8:
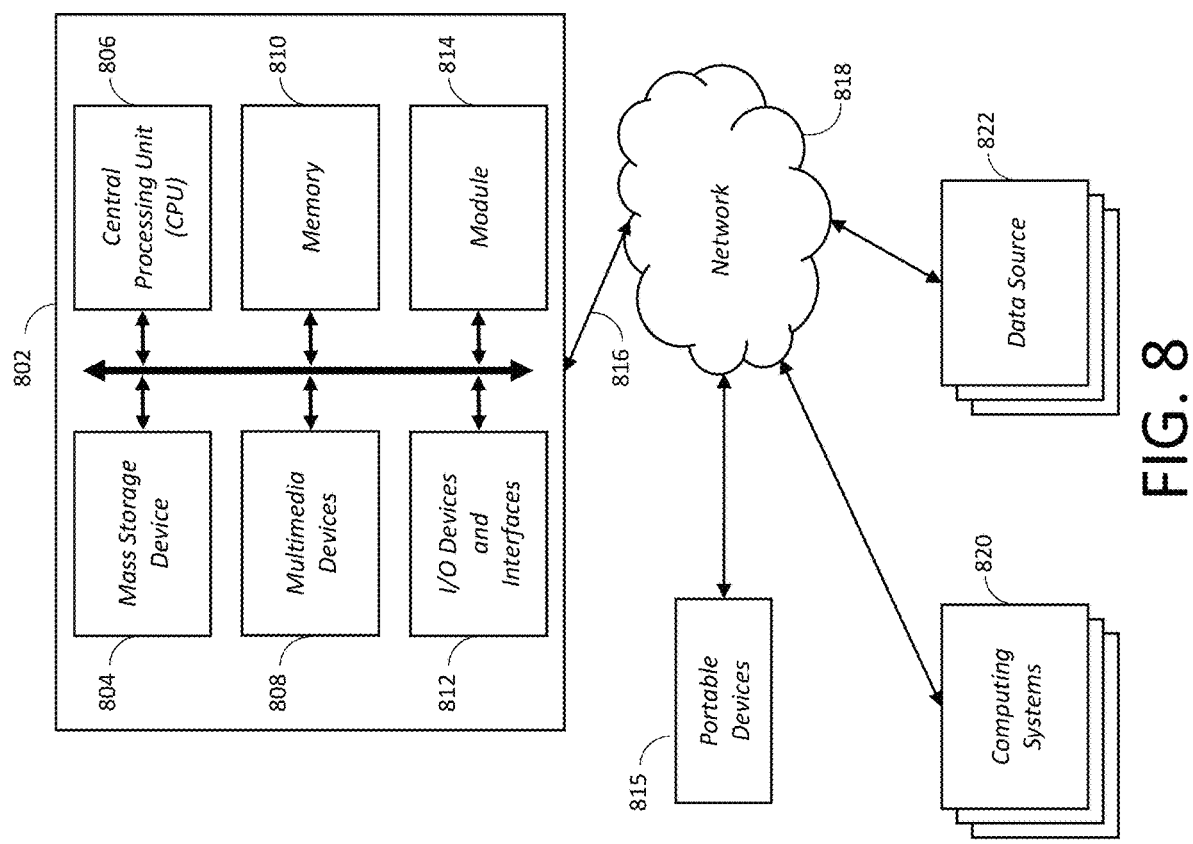
FIG. 8 illustrates a block diagram computer system of an embodiment of the present application.

Several implementations are discussed below in more detail in reference to the figures. FIG. 8 is a block diagram depicting an embodiment of a computer hardware system configured to run software for implementing one or more embodiments disclosed herein.

In some embodiments, the systems, processes, and methods described herein are implemented using a computing system, such as the one illustrated in FIG. 8. The example computer system 802 is in communication with one or more computing systems 820 and/or one or more data sources 822 via one or more networks 818. While FIG. 8 illustrates an embodiment of a computing system 802, it is recognized that the functionality provided for in the components and modules of computer system 802 can be combined into fewer components and modules, or further separated into additional components and modules.

The computer system 802 can comprise a module 814 that carries out the functions, methods, acts, and/or processes described herein. The module 814 is executed on the computer system 802 by a central processing unit 806 discussed further below.

In general, the word "module," as used herein, refers to logic embodied in hardware or firmware or to a collection of software instructions, having entry and exit points. Modules are written in a program language, such as JAVA, C or C++, Python, or the like. Software modules can be compiled or linked into an executable program, installed in a dynamic link library, or can be written in an interpreted language such as BASIC, PERL, LUA, or Python. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems and can be stored on or within any suitable computer readable medium or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 802 includes one or more processing units (CPU) 806, which can comprise a microprocessor. The computer system 802 further includes a physical memory 810, such as random-access memory (RAM) for temporary storage of information, a read only memory (ROM) for permanent storage of information, and a mass storage device 804, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 802 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 802 includes one or more input/output (I/O) devices and interfaces 812, such as a keyboard, mouse, touch pad, and printer. The I/O devices and interfaces 812 can include one or more display devices, such as a monitor, that allows the visual presentation of data to a user. More particularly, a display device provides for the presentation of GUIs as application software data, and multi-media presentations, for example. The I/O devices and interfaces 812 can also provide a communications interface to various external devices. The computer system 802 can comprise one or more multi-media devices 808, such as speakers, video cards, graphics accelerators, and microphones, for example.

The computer system 802 can run on a variety of computing devices, such as a server, a Windows server, a Structure Query Language server, a Unix Server, a personal computer, a laptop computer, and so forth. In other embodiments, the computer system 802 can run on a cluster computer system, a mainframe computer system and/or other computing system suitable for controlling and/or communicating with large databases, performing high volume transaction processing, and generating reports from large databases. The computing system 802 is generally controlled and coordinated by an operating system software, such as Windows XP, Windows Vista, Windows 7, Windows 8, Windows 10, Windows 11, Windows Server, Unix, Linux (and its variants such as Debian, Linux Mint, Fedora, and Red Hat), SunOS, Solaris, Blackberry OS, z/OS, iOS, macOS, or other operating systems, including proprietary operating systems. Operating systems control and schedule computer processes for execution, perform memory management, provide file system, networking, and I/O services, and provide a user interface, such as a graphical user interface (GUI), among other things.

The computer system 802 illustrated in FIG. 6 is coupled to a network 818, such as a LAN, WAN, or the Internet via a communication link 3116 (wired, wireless, or a combination thereof). Network 818 communicates with various computing devices and/or other electronic devices. Network 818 is communicating with one or more computing systems 820 and one or more data sources 822. The module 814 can access or can be accessed by computing systems 820 and/or data sources 822 through a web-enabled user access point. Connections can be a direct physical connection, a virtual connection, and other connection type. The web-enabled user access point can comprise a browser module that uses text, graphics, audio, video, and other media to present data and to allow interaction with data via the network 818.

Access to the module 814 of the computer system 802 by computing systems 820 and/or by data sources 822 can be through a web-enabled user access point such as the computing systems' 820 or data source's 822 personal computer, cellular phone, smartphone, laptop, tablet computer, e-reader device, audio player, or another device capable of connecting to the network 818. Such a device can have a browser module that is implemented as a module that uses text, graphics, audio, video, and other media to present data and to allow interaction with data via the network 818.

The output module can be implemented as a combination of an all-points addressable display such as a cathode ray tube (CRT), a liquid crystal display (LCD), a plasma display, or other types and/or combinations of displays. The output module can be implemented to communicate with input devices 812 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

The input device(s) can comprise a keyboard, roller ball, pen and stylus, mouse, trackball, voice recognition system, or pre-designated switches or buttons. The output device(s) can comprise a speaker, a display screen, a printer, or a voice synthesizer. In addition, a touch screen can act as a hybrid input/output device. In another embodiment, a user can interact with the system more directly such as through a system terminal connected to the score generator without communications over the Internet, a WAN, or LAN, or similar network.

In some embodiments, the system 802 can comprise a physical or logical connection established between a remote microprocessor and a mainframe host computer for the express purpose of uploading, downloading, or viewing interactive data and databases on-line in real time. The remote microprocessor can be operated by an entity operating the computer system 802, including the client server systems or the main server system, an/or can be operated by one or more of the data sources 822 and/or one or more of the computing systems 820. In some embodiments, terminal emulation software can be used on the microprocessor for participating in the micro-mainframe link.

In some embodiments, computing systems 820 who are internal to an entity operating the computer system 802 can access the module 814 internally as an application or process run by the CPU 806.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 802 can include one or more internal and/or external data sources (for example, data sources 822). In some embodiments, one or more of the data repositories and the data sources described above can be implemented using a relational database, such as Sybase, Oracle, CodeBase, DB2, PostgreSQL, and Microsoft® SQL Server as well as other types of databases such as, for example, a NoSQL database (for example, Couchbase, Cassandra, or MongoDB), a flat file database, an entity-relationship database, an object-oriented database (for example, InterSystems Cache), a cloud-based database (for example, Amazon RDS, Azure SQL, Microsoft Cosmos DB, Azure Database for MySQL, Azure Database for MariaDB, Azure Cache for Redis, Azure Managed Instance for Apache Cassandra, Google Bare Metal Solution for Oracle on Google Cloud, Google Cloud SQL, Google Cloud Spanner, Google Cloud Big Table, Google Firestore, Google Firebase Realtime Database, Google Memorystore, Google MongoDB Atlas, Amazon Aurora, Amazon DynamoDB, Amazon Redshift, Amazon ElastiCache, Amazon MemoryDB for Redis, Amazon DocumentDB, Amazon Keyspaces, Amazon Neptune, Amazon Timestream, or Amazon QLDB), a non-relational database, or a record-based database.

The computer system 802 can also access one or more databases 822. The databases 822 can be stored in a database or data repository. The computer system 802 can access the one or more databases 822 through a network 818 or can directly access the database or data repository through I/O devices and interfaces 812. The data repository storing the one or more databases 822 can reside within the computer system 802.

Additional Embodiments

In the foregoing specification, the systems and processes have been described with reference to specific embodiments thereof. It will, however, be evident that various modifications and changes may be made thereto without departing from the broader spirit and scope of the embodiments disclosed herein. The specification and drawings are, accordingly, to be regarded in an illustrative rather than restrictive sense.

Indeed, although the systems and processes have been disclosed in the context of certain embodiments and examples, it will be understood by those skilled in the art that the various embodiments of the systems and processes extend beyond the specifically disclosed embodiments to other alternative embodiments and/or uses of the systems and processes and obvious modifications and equivalents thereof. In addition, while several variations of the embodiments of the systems and processes have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosed systems and processes. Any methods disclosed herein need not be performed in the order recited. Thus, it is intended that the scope of the systems and processes herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and sub-combinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

It will also be appreciated that conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the embodiments are not to be limited to the particular forms or methods disclosed, but, to the contrary, the embodiments are to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (for example, as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (for example, as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C"

is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein but are to be accorded the widest scope consistent with this disclosure, the principles and the novel features disclosed herein.

We claim:

1. A computer-implemented method for remotely monitoring and managing a patient during the course of a medical treatment plan through the use of anthropometric measurements and three-dimensional (3D) models generated for the patient, wherein the computer-implemented method is performed by a computing system with steps comprising:
    receiving, from a user device of a patient, a first set of images of the patient captured using a camera of the user device during a first imaging session at a first point in time, wherein the patient is enrolled in a medical treatment plan that involves self-administration of a dosage of a selected weight loss drug, and wherein the first set of images of the patient comprises images of various body regions of the patient from multiple angles, wherein to capture the first set of images, the computer-implemented method is configured to:
        instruct the patient to move in one or more directions based on a determination that a portion of a body of the patient or an entirety of the body of the patient is not in view of the camera; and
        generate an augmented reality view for display to the patient, the augmented reality view comprising at least the view of the camera and a computer-generated graphic that instructs the patient regarding position of the patient;
    generating a first 3D model of the patient by processing the first set of images of the patient, wherein the first 3D model represents the patient's body during the first imaging session;
    generating a user skeleton for the first 3D model based on motion of the patient detected in the first set of images, wherein the user skeleton identifies location of the patient's joints, and wherein the user skeleton provides static-over-time reference points for anthropometric measurements;
    calculating a first anthropometric measurement for the patient based on the first 3D model and a reference point from the user skeleton, wherein the first anthropometric measurement is associated with the patient's body during the first imaging session;
    initiating a virtual proctoring session between the patient and a proctor, wherein during the virtual proctoring session the proctor is provided with a live video stream of the patient self-administering the dosage of the weight loss drug;
    based on the virtual proctoring session, determining that the patient is compliant with the medical treatment plan;
    receiving, from the user device of patient, a second set of images of the patient captured using the camera of the user device during a second imaging session at a second point in time, wherein the second set of images of the patient comprises images of various body regions of the patient from multiple angles;
    generating a second 3D model of the patient by processing the second set of images of the patient, wherein the second 3D model represents the patient's body during the second imaging session;
    mapping the user skeleton to the second 3D model, such that the user skeleton continues to provide static-over-time reference points for anthropometric measurements;
    calculating a second anthropometric measurement for the patient based on the second 3D model and the reference point from the user skeleton, wherein the second anthropometric measurement is associated with the patient's body during the second imaging session;
    comparing the first anthropometric measurement against the second anthropometric measurement to determine an observed change in the patient between the first point in time and the second point in time; and
    based on the observed change in the patient, determining an adjustment to adjusting the dosage of the weight loss drug administered in the medical treatment plan.

2. The computer-implemented method of claim 1, further comprising:
    based on the second 3D model of the patient, generating a predictive 3D model of the patient that models and predicts the patient's body at a future point in time because of continued adherence to the medical treatment plan.

3. The computer-implemented method of claim 1, wherein the observed change in the patient is a reduction in weight of the patient, a reduction in BMI of the patient, or a reduction in waist circumference of the patient.

4. The computer-implemented method of claim 1, wherein the first and second set of images of the patient comprise images of the patient in a set of poses.

5. The computer-implemented method of claim 1, further comprising:
    sending, to the user device of the patient, an electronic message with a behavioral recommendation associated with the medical treatment plan.

6. The computer-implemented method of claim 1, further comprising:
    receiving information about the patient; and
    applying an artificial intelligence system to the information about the patient to select the weight loss drug and generate the medical treatment plan for the patient.

7. The computer-implemented method of claim 1, wherein the virtual proctoring session is part of a series of virtual proctoring sessions scheduled for the patient as periodic check-ins under the medical treatment plan.

8. The computer-implemented method of claim 1, further comprising:
    generating an electronic prescription with the adjusted dosage of the weight loss drug; and
    sending the electronic prescription to a pharmacy.

9. The computer-implemented method of claim 1, further comprising:
    sending, to the user device of the patient, a message containing a link for attending the virtual proctoring session.

10. The computer-implemented method of claim 1, further comprising:
    sending, to the user device of the patient, a message indicating the dosage of the weight loss drug has been adjusted.

11. A non-transitory computer-readable medium storing instructions for a computer-implemented method for remotely monitoring and managing a patient during the course of a medical treatment plan through the use of anthropometric measurements and three-dimensional (3D) models generated for the patient, the computer-implemented method comprising:
receiving, from a user device of a patient, a first set of images of the patient captured using a camera of the user device during a first imaging session at a first point in time, wherein the patient is enrolled in a medical treatment plan that involves self-administration of a dosage of a selected weight loss drug, and wherein the first set of images of the patient comprises images of various body regions of the patient from multiple angles, wherein to capture the first set of images, the computer-implemented method is configured to:
instruct the patient to move in one or more directions based on a determination that a portion of a body of the patient or an entirety of the body of the patient is not in view of the camera; and
generate an augmented reality view for display to the patient, the augmented reality view comprising at least the view of the camera and a computer-generated graphic that instructs the patient regarding position of the patient;
generating a first 3D model of the patient by processing the first set of images of the patient, wherein the first 3D model represents the patient's body during the first imaging session;
generating a user skeleton for the first 3D model based on motion of the patient detected in the first set of images, wherein the user skeleton identifies location of the patient's joints, and wherein the user skeleton provides static-over-time reference points for anthropometric measurements;
calculating a first anthropometric measurement for the patient based on the first 3D model and a reference point from the user skeleton, wherein the first anthropometric measurement is associated with the patient's body during the first imaging session;
initiating a virtual proctoring session between the patient and a proctor, wherein during the virtual proctoring session the proctor is provided with a live video stream of the patient self-administering the dosage of the weight loss drug;
based on the virtual proctoring session, determining that the patient is compliant with the medical treatment plan;
receiving, from the user device of patient, a second set of images of the patient captured using the camera of the user device during a second imaging session at a second point in time, wherein the second set of images of the patient comprises images of various body regions of the patient from multiple angles;
generating a second 3D model of the patient by processing the second set of images of the patient, wherein the second 3D model represents the patient's body during the second imaging session;
mapping the user skeleton to the second 3D model, such that the user skeleton continues to provide static-over-time reference points for anthropometric measurements;
calculating a second anthropometric measurement for the patient based on the second 3D model and the reference point from the user skeleton, wherein the second anthropometric measurement is associated with the patient's body during the second imaging session;
comparing the first anthropometric measurement against the second anthropometric measurement to determine an observed change in the patient between the first point in time and the second point in time; and
based on the observed change in the patient, determining an adjustment to the dosage of the weight loss drug administered in the medical treatment plan.

12. The non-transitory computer-readable medium of claim 11, wherein the computer-implemented method further comprises:
based on the second 3D model of the patient, generating a predictive 3D model of the patient that models and predicts the patient's body at a future point in time because of continued adherence to the medical treatment plan.

13. The non-transitory computer-readable medium of claim 11, wherein the observed change in the patient is a reduction in weight of the patient, a reduction in BMI of the patient, or a reduction in waist circumference of the patient.

14. The non-transitory computer-readable medium of claim 11, wherein the first and second set of images of the patient comprise images of the patient in a set of poses.

15. The non-transitory computer-readable medium of claim 11, wherein the computer-implemented method further comprises:
sending, to the user device of the patient, an electronic message with a behavioral recommendation associated with the medical treatment plan.

16. The non-transitory computer-readable medium of claim 11, wherein the computer-implemented method further comprises:
receiving information about the patient; and
applying an artificial intelligence system to the information about the patient to select the weight loss drug and generate the medical treatment plan for the patient.

17. The non-transitory computer-readable medium of claim 11, wherein the virtual proctoring session is part of a series of virtual proctoring sessions scheduled for the patient as periodic check-ins under the medical treatment plan.

18. The non-transitory computer-readable medium of claim 11, wherein the computer-implemented method further comprises:
generating an electronic prescription with the adjusted dosage of the weight loss drug; and
sending the electronic prescription to a pharmacy.

19. The non-transitory computer-readable medium of claim 11, wherein the computer-implemented method further comprises:
sending, to the user device of the patient, a message containing a link for attending the virtual proctoring session.

20. The non-transitory computer-readable medium of claim 11, wherein the computer-implemented method further comprises:
sending, to the user device of the patient, a message indicating the dosage of the weight loss drug has been adjusted.

* * * * *